(12) United States Patent
Choi et al.

(10) Patent No.: US 10,130,668 B2
(45) Date of Patent: *Nov. 20, 2018

(54) **COMPOSITION COMPRISING *DENDROPANAX MORBIFERA* EXTRACT OR COMPOUND DERIVED THEREFROM AS ACTIVE INGREDIENT FOR PREVENTING AND TREATING BENIGN PROSTATIC HYPERPLASIA**

(71) Applicant: INDUSTRY-ACADEMIC COOPERATION FOUNDATION, CHOSUN UNIVERSITY, Gwangju (KR)

(72) Inventors: Cheol-Hee Choi, Gwangju (KR); Young-Sook Moon, Gwangju (KR); Ju-Hee Han, Gwangju (KR); Kyoung-In Lee, Gwangju (KR); Hyun-Jung Kim, Jeollanam-do (KR)

(73) Assignee: Industry-Academic Cooperation Foundation, Chosun University (KR)

( * ) Notice: Subject to any disclaimer, the term of this patent is extended or adjusted under 35 U.S.C. 154(b) by 854 days.

This patent is subject to a terminal disclaimer.

(21) Appl. No.: 14/414,883

(22) PCT Filed: Jan. 30, 2013

(86) PCT No.: PCT/KR2013/000766
§ 371 (c)(1),
(2) Date: Jan. 14, 2015

(87) PCT Pub. No.: WO2014/014177
PCT Pub. Date: Jan. 23, 2014

(65) Prior Publication Data
US 2015/0182571 A1    Jul. 2, 2015

(30) Foreign Application Priority Data

Jul. 18, 2012  (KR) .................. 10-2012-0078103
Jan. 7, 2013   (KR) .................. 10-2013-0001478

(51) Int. Cl.
*A61K 36/25*    (2006.01)
*A23L 33/105*   (2016.01)

(52) U.S. Cl.
CPC ............ *A61K 36/25* (2013.01); *A23L 33/105* (2016.08)

(58) Field of Classification Search
None
See application file for complete search history.

(56) References Cited

FOREIGN PATENT DOCUMENTS

| KR | 10-2000-004499 | 1/2000 |
| KR | 10-2004-0107853 | 12/2004 |
| KR | 10-2006-0131360 | 12/2006 |

OTHER PUBLICATIONS

Choi, Y.H., "Studies on the Isolation and Analysis of Korean Golden Varnish (Hwangchil) Exudates of *Dendropanax morbifera*Lev.," Hanbat National University, Dec. 2003 (English Abstract).
Park, et al., "Isolation and anticomplement activity of compounds from *Dendropanax morbifera*," J. of Ethnopharmacology, 90:403-408, 2004.
Yu, et al., "Oleifolioside A, a New Activie Compound, Attenuates LPS-Stimulated iNOS and COX-2 Expression through the Downregulation of NF-[Kappa]B and MAPK Activities in RAW 264.7 Macrophages," Evidence-Based Complementary and Alternative Medicine, vol. 2012, Article ID 637512, May 30, 2012.
Wu, et al., "Synthesis and Biological Evaluation of Novel Thiazolidmediane Analogues as 15-Hydroxyprostaglandin Dehyrogenase Inhibitors," Journal of Medicinal Chemistry, 54:5260-5264, 2011.
Choi, et al., "Control of the intracellular levels of prostaglandin $E_2$ through inhibition of the 15-hydroxyprostaglandin dehydrogenase for wound healing," Bioorganic & Medicinal Chemistry 21:4477-4484, 2013.

*Primary Examiner* — Terry A McKelvey
*Assistant Examiner* — Catheryne Chen
(74) *Attorney, Agent, or Firm* — JHK Law; Joseph Hyosuk Kim

(57) ABSTRACT

Provided is a use of *Dendropanax morbifera* extract as an agent for preventing and treating benign prostatic hyperplasia, and more particularly, a composition for preventing and treating benign prostatic hyperplasia and a functional health food for preventing and reducing the effects of benign prostatic hyperplasia, in which the composition and food include, as an active ingredient, a *Dendropanax morbifera* extract or a compound which is isolated from the extract and then purified.

9 Claims, 21 Drawing Sheets

COMPOSITION COMPRISING *DENDROPANAX MORBIFERA* EXTRACT OR COMPOUND DERIVED THEREFROM AS ACTIVE INGREDIENT FOR PREVENTING AND TREATING BENIGN PROSTATIC HYPERPLASIA

TECHNICAL FIELD

The present invention relates to a composition including a *Dendropanax morbifera* extract or a compound derived from the *Dendropanax morbifera* extract as an active ingredient for preventing and treating benign prostatic hyperplasia

BACKGROUND ART

As one of the most commonly found diseases in male, recently the occurrence of benign prostatic hyperplasia (BPH) is on the sharp rise. Approximately 50% of people in 60s and 90% of people who are older than 85 are known to have BPH and normally they have lower urinary tract symptoms (LUTS) such as nocturia, hesitancy, urinary frequency, and urinary incontinence and surgery is required if urinary tract infection and urinary tract obstruction occur repeatedly (Bertaccini, Vassallo et al. 2001; Wei, Calhoun et al. 2005). As a consequence, even though BPH is not a lethal disorder, it is emerging as an important medical problem of the current aging society as it degrades the quality of life.

Generally, the size of prostate of an adult is around 20 g (±6 g), but, it can grow as large as 40 to 400 g once it becomes abnormal (Foster 2000; Thorpe and Neal 2003). BPH, a histologic disease, in which the prostate is overgrown due to increased number of normal prostatic cells, causes LUTS if an overgrown prostate presses proximal urethra (Jacobsen, Girman et al. 2001; Thorpe and Neal 2003; Liu, Lee et al. 2006). Particularly, BPH induces dramatic changes on stromal cells in the area surrounding the prostatic transition zone and proximal urethra (Foster 2000; Committee 2003), and the ratio of stromal cell to epithelial cell is 2.7:1 in normal condition, whereas it is 4.6:1, once symptom of BPH is present (Foster 2000). The growth of these stromal cells is regulated by adrenergic nerve system and ala subtype receptor is known to be the most predominantly found adrenergic receptor in the prostatic stromal tissue (Foster 2000; Thorpe and Neal 2003).

Meanwhile, although the cause of BPH has never been clearly identified, it is known to be caused by change in male sex hormone due to aging (Isaacs and Coffey 1989). In case of normal prostate, epithelial cell and stromal cell closely interact and thereby the growth and regression of prostate are organically regulated, but in case of BPH, the volume of prostate becomes larger due to rarer apoptosis. Particularly, there are some reports that epidermal growth factor (EGF), basic fibroblast growth factor (bFGF) and transforming growth factor $\beta$ (TGF-$\beta$) are involved. EGF or TGF-$\beta$ is strong mitosis-stimulating factor and it is believed that EGF mediates the androgen-induced prostatic hyperplasia because a large amount of EGF is included in the prostatic tissues or prostatic secretion (Lee 1996). TGF-$\beta$ is also increased in the individual having BPH and presumably it is thought to be involved in differentiation of matrix cell into smooth muscle cell (Klinger, Bretland et al. 1999). bFGF is a strong mitosis-stimulating factor that is overexpressed for BPH. bFGF is formed in both of stromal cell and epithelial cell and admittedly, it is reported as the most important factor responsible for the lesion of BPH (Saez, Gonzalez-Baena et al. 1999).

Testosterone and its active form, 5$\alpha$-dihydroxytestosterone (DHT) also play as an important role for BPH. The DHT, which is formed from testosterone by 5$\alpha$-reductase type 2, is abundantly found for BPH and it is reported that both testosterone and DHT stimulates the growth of stromal cells in the prostate (Lee, Seong et al. 2001; Thorpe and Neal 2003). Besides, a number of studies are in progress lately in order to confirm the causes of BPH that are associated with dietary intake, exercise, and metabolic diseases (Parsons 2007).

While surgery was conducted as the most commonly practiced method of clinical treatment for BPH in the past, since the late 1980s, clinical treatment has been rapidly diverted to drug administration (Milroy 1990). Nowadays there are $\alpha$-adrenergic receptor antagonist ($\alpha$-blockers), 5$\alpha$-reductase inhibitor, and phytotherapy that are used as remedial drug to treat BPH. In the early stage, monotherapy was conducted, in which drugs are administered to patients and proper drug is chosen and administered to each patient for the purpose of extending the remaining time until surgery by relieving the symptom, but combined treatment was also conducted, in which $\alpha$-blockers and 5$\alpha$-reductase inhibitors are co-administered. The drug $\alpha$-blockers have benefit as they show effects instantly by immediately relieving the symptoms and 5$\alpha$-reductase inhibitors have benefit as they delay the progression of disease for long, although immediate effects are scarcely shown. As currently used $\alpha$-blockers, there are alfuzosin, doxazosin, tamsulosin and terzosin. While above four have nearly identical effectiveness, side effects are reported to be different from one another (Committee 2003). $\alpha$-blockers block the $\alpha$1-adrenergic receptors that are abundantly expressed in prostate and bladder neck. When $\alpha$1-adrenergic receptors are blocked, prostatic muscles are relaxed and thereby urination and other symptoms of LUTS are relieved and subsequently the bladder dysfunction caused by BPH can be eliminated (Wykretowicz, Guzik et al 2008). As the most common side effects of this drug, there are dizziness, asthenia, nasal congestion, and orthostatic hypotension (Committee 2003). Dutasteride and finasteride that are used as 5$\alpha$-reductase inhibitor function in different mechanisms from that of $\alpha$-blocker. The dutasteride inhibits both 5$\alpha$-reductase type 1 (mostly expressed in liver and skin) and type 2 (mostly expressed in reproductive organ), whereas the finasteride only inhibits type 2. These mechanisms of action of drugs inhibit the formation of DHT by competing with 5$\alpha$-reductase. As the abnormal growth of prostate depends on the amount of DHT, the size of prostate is reduced once the amount of DHT is decreased and diseases associated with the BPH can be prevented accordingly (McConnell, Roehrborn et al. 2003). However, it requires 2 month to 1 year of treatment until the accompanied diseases are improved by relying on this drug to reduce the size of prostate (Gormley, Stoner et al. 1992; Kirby, Bryan et al. 1992; Roehrborn, Boyle et al. 2002). Furthermore, erectile dysfunction, hyposexuality, ejaculatory dysfunction and hypertrophy of breast in male may occur as side effects and 3 months after stopping the administration, condition regresses to what it was prior to the treatment. Currently, there are some reports that it is more effective to use the finasteride, a widely administered drug when the size of prostate is larger than 40 g and thus, in case of prescribing this drug, PSA (prostate specific antigen) that is used as the screening factor for prostate cancer is tested beforehand.

Also, it is known that combined therapy is more effective if the size of prostate is larger than 40 g and PSA is higher than 4 ng/mL (Committee 2003).

Besides, plant-derived alternative medicines are widely used to treat BPH, and for example, there are saw palmetto, pumpkin seeds, and nettle root.

Although there are a number of therapeutic drugs commensurate with the importance of benign prostatic hyperplasia, due to the limited effectiveness and concerns of side effects such as erectile dysfunction once androgen signaling is inhibited, development of a brand new therapeutic agent that has negligible side effect and confer a fundamental therapeutic effect is urgently required.

One of the prevention and treatment methods of erectile dysfunction is to rely on the blood flow improvement effect of prostaglaind (Wolfson B, Pickett S, Scott N E, DeKernion J B, Rajfer J. 1993 July; 42(1):73-5; Karabulut A, PeL, OzkardeH, AltuU, Erol D. Urol Int 2001; 67(2):160-2). While 15-PGDH is induced by testosterone and DHT in LNCaP cell, an androgen-dependent prostate cancer cell line in a concentration and time dependent fashion, the same result was not observed in PC3 cells, an androgen-independent prostate cancer cell line (Tong M, Tai H H. 2000 Sep. 16; 276(1):77-81). Therefore, if a substance that inhibits androgen signaling can increase the blood flow in the penis by inhibiting the expression or the activity of 15-PGDH and by increasing prostaglandin E2, it is highly possible to reduce the side effect of erectile dysfunction.

Therefore, in the present invention, a *Dendropanax morbifera* extract was identified to have anti-androgen effect in, an androgen-dependent prostate cancer cell line and based on the idea, in which the side effect of erectile dysfunction can be relieved when the blood flow of the penis is increased by increasing prostaglandin E2 through inhibiting the expression of 15-PGDH, a target gene of androgen receptor, the present invention was finally completed by confirming that the composition including a *Dendropanax morbifera* hexane extract or a compound derived from the above-described extract is effective for the treatment and prevention of BPH in animal model with BPH induced by testosterone.

DISCLOSURE

Technical Problem

Therefore, an object of the present invention is to provide a composition including a *Dendropanax morbifera* extract as an active ingredient for preventing and treating benign prostatic hyperplasia.

Additionally, another object of the present invention is to provide a health functional food including a *Dendropanax morbifera* extract as an active ingredient for preventing and relieving benign prostatic hyperplasia.

Moreover, another object of the present invention is to provide a pharmaceutical composition including a 9,16S-dihydroxy-10,17-octadecadiene-12,14-diynoic acid, 9,16R-dihydroxy-10,17-octadecadiene-12,14-diynoic acid, or (9Z)-16-hydroxy-9,17-octadecadiene-12,14-diynoic acid compound, which are isolated and purified from the above-described *Dendropanax morbifera* extract, as an active ingredient for preventing and treating benign prostatic hyperplasia.

Moreover, the object of the present invention is to provide a pharmaceutical composition including a *Dendropanax morbifera* extract, a 9,16S-dihydroxy-10,17-octadecadiene-12,14-diynoic acid, 9,16R-dihydroxy-10,17-octadecadiene-12,14-diynoic acid, or (9Z)-16-hydroxy-9,17-octadecadiene-12,14-diynoic acid compound, which are isolated and purified from the above-described *Dendropanax morbifera* extract, as an active ingredient for preventing and treating prostate cancer.

Technical Solution

In order to resolve the problems above, the present invention provides a pharmaceutical composition including a *Dendropanax morbifera* extract as an active ingredient for preventing and treating benign prostatic hyperplasia.

In one exemplary embodiment of the present invention, the above-described *Dendropanax morbifera* extract may be a crude extract of *Dendropanax morbifera*, a polar solvent soluble extract or a non-polar solvent soluble extract.

In one exemplary embodiment of the present invention, the above-described crude extract of *Dendropanax morbifera* may be an extract that is soluble in any solvent selected from water including purified water, methanol, ethanol, butanol or a mixed solvent thereof.

In one exemplary embodiment of the present invention, the above-described non-polar solvent soluble extract may be an extract that is soluble in hexane, chloroform, dichloromethane, or ethyl acetate.

In one exemplary embodiment of the present invention, the above-described *Dendropanax morbifera* extract may have inhibitory activity for expression of 5α-reductase or androgen receptor (AR).

In one exemplary embodiment of the present invention, the *Dendropanax morbifera* extract may include a 9,16S-dihydroxy-10,17-octadecadiene-12,14-diynoic acid, 9,16R-dihydroxy-10,17-octadecadiene-12,14-diynoic acid, or (9Z)-16-hydroxy-9,17-octadecadiene-12,14-diynoic acid compound.

Furthermore, the present invention provides a pharmaceutical composition including a 9,16S-dihydroxy-10,17-octadecadiene-12,14-diynoic acid, 9,16R-dihydroxy-10,17-octadecadiene-12,14-diynoic acid, or (9Z)-16-hydroxy-9,17-octadecadiene-12,14-diynoic acid compound as an active ingredient for preventing and treating benign prostatic hyperplasia.

In one exemplary embodiment of the present invention, the above-described compound may be isolated and purified from a *Dendropanax morbifera* hexane extract.

In one exemplary embodiment of the present invention, the above-described compound may have activity of inhibiting and reducing the mRNA expressions of PSA (prostate specific antigen), 15-PGDH, 5αR-1 (5α-reductase type 1) and 5αR-2 (5α-reductase type 2).

Furthermore, the present invention provides a health functional food including a *Dendropanax morbifera* extract as an active ingredient for preventing and relieving benign prostatic hyperplasia.

In one exemplary embodiment of the present invention, the above-described *Dendropanax morbifera* extract may include a 9,16S-dihydroxy-10,17-octadecadiene-12,14-diynoic acid, 9,16R-dihydroxy-10,17-octadecadiene-12,14-diynoic acid, or (9Z)-16-hydroxy-9,17-octadecadiene-12,14-diynoic acid compound.

In one exemplary embodiment of the present invention, the above-described food can be selected from the group consisting of beverages, meat, chocolates, foods, snacks, pizza, instant noodles, other noodles, chewing gums, candies, ice creams, alcohol beverages, vitamin complexes and health supplemental foods.

Furthermore, the present invention provides a pharmaceutical composition including a *Dendropanax morbifera* extract, a 9,16S-dihydroxy-10,17-octadecadiene-12,14-diynoic acid, 9,16R-dihydroxy-10,17-octadecadiene-12,14-diynoic acid, or (9Z)-16-hydroxy-9,17-octadecadiene-12,14-diynoic acid compound, which is isolated and purified from the above-described *dendropanax morbifera* extract, as an active ingredient for preventing and treating prostate cancer.

Advantageous Effects

The present invention relates to a composition including a *Dendrapanax morbifera* extract as an active ingredient for treating and preventing benign prostatic hyperplasia and a health functional food including a *Dendrapanax morbifera* extract as an active ingredient for preventing and relieving benign prostatic hyperplasia. The *Dendrapanax morbifera* extract according to the present invention was identified to be effective in preventing and treating benign prostatic hyperplasia through the mechanism of inhibiting the androgen receptor signaling that induces benign prostatic hyperplasia and furthermore, it was confirmed to be safe for cells as no cytotoxicity is induced. Therefore, the *Dendrapanax morbifera* extract according to the present invention can be useful to produce the pharmaceutical products and functional foods for preventing, treating and relieving benign prostatic hyperplasia.

MODES OF THE INVENTION

Figure 1:
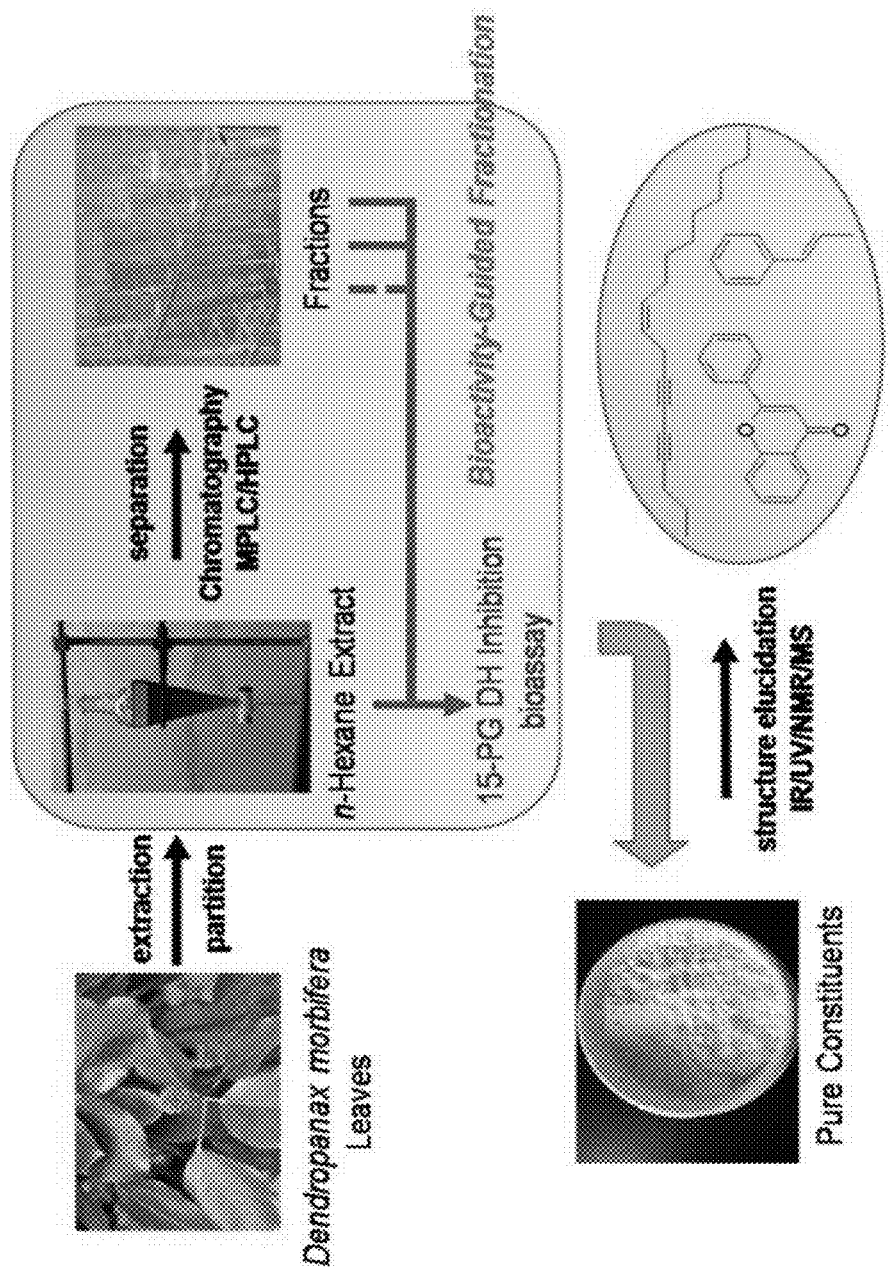
FIG. 1 is a schematic diagram illustrating the process for preparing a *Dendrapanax morbifera* extract according to the present invention.

The definitions of terms used in the present invention are as follows.

The term, "extract" is a crude extract of *Dendropanax morbifera*, a polar solvent soluble extract, or a non-polar solvent soluble extract.

The term, "crude extract" includes an extract that is soluble in a solvent selected from water including purified water, lower alcohols having 1 to 4 carbon atoms such as methanol, ethanol, and butanol, or a mixed solvent thereof, preferably soluble in water and methanol-mixed solvent, and more preferably soluble in 50% to 100% methanol.

The term, "polar solvent soluble extract" includes an extract that is soluble in a solvent selected from water, methanol, butanol or a mixed solvent thereof, preferably soluble in water or methanol, and more preferably soluble in methanol.

The term, "non-polar solvent soluble extract" includes an extract that is soluble in hexane, chloroform, dichloromethane, or ethyl acetate, preferably soluble in hexane, dichloromethane, or ethyl acetate, and more preferably soluble in hexane or ethyl acetate.

The term, "pharmaceutical composition" means mixture of the *Dendropanax morbifera* extract of the present invention and other chemical components such as diluent or carrier.

The term, "carrier" is defined as a compound that facilitates the migration of compounds into the cells or tissues. For example, dimethylsulfoxide (DMSO) is a carrier that is commonly used to facilitate the penetration of a number of organic compounds into the cells or tissues of organisms.

The term, "diluents" is defined as a compound that not only stabilizes the biologically active form of target compounds, but also a compound that is diluted in water in which the compounds are dissolved. The salts dissolved in buffer solution are used as diluents in the related art. A commonly used buffer solution is phosphate buffered saline solution, because it mimics the condition of salts in human solution. Since the buffered salts are capable of controlling the pH of solution at a low concentration, the biological activity of compounds are rarely altered by buffer diluents.

The term, "effective amount" is the adequate amount that has influence on beneficial or desired clinical or biochemical results. The effective amount can be administered once or more. For the object of the present invention, the effective amount is the amount appropriate to temporarily relieve, improve, stabilize, reverse, slow or delay the progression of diseased states.

Hereinafter, the present invention will be described in detail.

The all technical terms used herein, unless otherwise defined, have the identical meaning as commonly understood by one of ordinary skill in the related art to which the present invention belongs. Moreover, although desired methods or reagents were stated in the present specification, anything similar or equivalent to these are included in the scope of the present invention. The all publications and contents thereof referenced herein are introduced to the present invention.

The present invention relates to a use of *Dendropanax morbifera* extract, and a particular physiological activity and function of the *Dendropanax morbifera* extract.

The *Dendropanax morbifera* LEV., which is a member of Japanese *angelica* trees, an evergreen broad-leaved tree, is an indigenous species of trees to Korea that grows naturally in Jeju-do, and southwestern coastal areas of Korea such as Wan-do, Bogil-do, Haenam. The clove component included in *Dendropanax morbifera* contains a small amount of terpene and a large amount of sesquiterpen, and despite of differences dependent on the collection period or place, germacrene-d, β-selinene, α-amorphene, α-selinene, δ-cadinene, γ-cadinene, T-muurolol, β-elemene, bicycle[4,4,0]dec-1-en-2-isopropyl-5-methyl-9-methylene, β-cadinene, germacrene-B, α-copaene, α-humulene, α-cadinene, and a small amount of linalool L, α-terpinene, α-cubebene, α-ylangene, (+)-calarene, 3,7-guaiadine, (−)-isoledene, β-cubebene, limonene, aromadendrene, cadina-1,4-diene, and the like, are included.

Although there is no limitation on the parts of *Dendropanax morbifera* LEV., such as, leaf, stem, and bark that may be used for the present invention, it is preferable to use the leaf.

The *Dendropanax morbifera* extract may be produced by methods known in the related art, the modified methods thereof, or the methods of the present invention. As one specific example, it may be produced by the method described below.

The *Dendropanax morbifera* extract or crude extract of the present invention may be obtained by adding the solvent selected from water including purified water, lower alcohols with 1 to 4 carbon atoms such as methanol, ethanol, and butanol, or a mixed solvent thereof, preferably the mixed solvent of water and ethanol, and more preferably 50 to 100% ethanol, in the volume of about 1 to 30 times with respect to the weight of *Dendropanax morbifera* LEV., preferably the volume (w/v %) of 5 to 15 times with respect to the weight of *Dendropanax morbifera* LEV., and then by extracting at about 0 to 100° C., preferably at room temperature for 10 to 60 hours, preferably by using extraction methods, such as, cold extraction, hot water extraction, ultrasonic extraction, reflux cooling extraction, or heating extraction for 30 to 50 hours, and preferably by hot water extraction followed by filtering and vacuum evaporation.

Furthermore, the polar or non-polar solvent soluble extract of the present invention may be obtained by dispersing water with a weight by volume of the crude extract obtained by the method described above, preferably by dispersing water in the volume of about 1 to 150 times with respect to the weight of 50 to 100% ethanol crude extract, preferably the volume of 5 to 100 times (w/v %), and then, by adding hexane, ethyl acetate and butanol in order in the volume of about 1 to 10 times with respect to the volume of water, preferably the volume of 1 to 5 times, and fractionating 1 to 5 times, preferably by fractionating 2 to 4 times. Preferably, the hexane extract may be obtained and used.

The concentrate of the above-described extract may be obtained in a type of powder either by lysophilization at −80° C. or vacuum decompression at 50° C.

The present invention includes a method of preparing the *Dendropanax morbifera* extract. The above-described preparation method is no more one exemplary method thereof, but may be adequately modified by a variety of methods based on the technology in the related art, and then, used. For example, an extraction method not exemplified according to the present invention can be successfully conducted by a skilled person in the related art through clear modification.

For anyone who has common knowledge of the related art to which the present invention belongs, it is possible to find out the detailed reaction condition for preparation of *Dendropanax morbifera* extract of the present invention through the exemplary embodiments described later, and thus, the detailed description thereabout will not be provided.

Meanwhile, the present invention identified that the *Dendropanax morbifera* extract of the present invention possesses anti-androgen activity by which the protein synthesis of AR is inhibited, namely, it was confirmed that the *Dendropanax morbifera* extract of the present invention is involved in inhibition of AR signaling. 5α-reductase is an important enzyme that accelerates AR signaling by transforming testosterone to 5α dihydroxytestosterone (DHT), and 5α-reductase inhibitors are used to treat benign prostatic hyperplasia.

In this regard, the *Dendropanax morbifera* extract of the present invention inhibits AR signaling by reducing the gene expressions of 5α-reductase 1 and 2, and AR and by blocking the AR receptor, and particularly, given that excessively synthesized DHT is combined with AR in the prostatic cells, and causes benign prostatic hyperplasia and even prostate cancer. Therefore, it is possible that the *Dendropanax morbifera* extract of the present invention may prevent and treat benign prostatic hyperplasia through the mechanism of AR signaling inhibition.

Moreover, the present invention confirmed that the *Dendropanax morbifera* extract has anti-androgen effect in LNCaP•FGC, an androgen dependent prostate cancer cell line and increases prostaglandin $E_2$ by inhibiting the gene expression of 15-PGDH, a target gene of androgen receptor.

For side effects of androgen inhibitor that inhibits androgen signaling pathway, there are some reports on the occurrence of erectile dysfunction, and recently, Dr. Abdulmagate Traish, a physician of urology department at Boston University school of medicine in the United States reported that Avodart (dutasteride), and Proscar and Propecia (finasteride), which are therapeutic agents used for treatment of benign prostatic hyperplasia by inhibiting male sex hormone androgen, may cause erectile dysfunction and for some patients, erectile dysfunction cannot be recovered even after stopping the administration thereof (Traish A M, 2011 March; 8(3):872-84).

Meanwhile, the *Dendropanax morbifera* extract of the present invention may reduce the previously held concerns for side effects of erectile dysfunction, because it inhibits the gene expression of 15-PGDH, the target gene of androgen receptor and increases the level of prostaglandin $E_2$ and thereby increases the blood flow in penis.

In addition, the *Dendropanax morbifera* extract of the present invention inhibits the gene expression of 5α-reductase and protein synthesis of androgen receptor (AR), and confers no toxicities in experimental animals, and thus, based on such molecular mechanisms, it may be useful for prevention and treatment of benign prostatic hyperplasia.

Furthermore, the present inventors identified the treatment effect of *Dendropanax morbifera* extract for benign prostatic hyperplasia, and isolated and purified the active ingredient in order to identify the pharmacological active ingredient included in the above-described extract.

As a consequence, according to one exemplary embodiment of the present invention, the single compounds of 9,16S-dihydroxy-10,17-octadecadiene-12,14-diynoic acid (HS3), 9,16R-dihydroxy-10,17-octadecadiene-12,14-diynoic acid (HS5), and (9Z)-16-hydroxy-9,17-octadecadiene-12,14-diynoic acid (HS7) were isolated and purified from a *Dendropanax morbifera* hexane extract, and it was identified that the above-described compounds are effective in inhibiting mRNA expression of PSA in AR signaling, which is a signal transmitting mechanism involved in benign prostatic hyperplasia and prostate cancer and also the mRNA expression of 1 5αR-1/-2 is inhibited as well as the mRNA expression of 15-PGDH.

Therefore, the inventors of the present invention identified that not only the *Dendropanax morbifera* extract of the present invention but also the 9,16S-dihydroxy-10,17-octadecadiene-12,14-diynoic acid (HS3), 9,16R-dihydroxy-10,17-octadecadiene-12,14-diynoic acid (HS5), and (9Z)-16-hydroxy-9,17-octadecadiene-12,14-diynoic acid (HS7) compound that are contained in the above-described extract may be used as a therapeutic agent for treatment of benign prostatic hyperplasia and prostate cancer.

Hence, the present invention may provide a pharmacological composition including a *Dendropanax morbifera* extract as an active ingredient as well as a pharmaceutical composition including a 9,16S-dihydroxy-10,17-octadecadiene-12,14-diynoic acid (HS3), and 9,16R-dihydroxy-10,17-octadecadiene-12,14-diynoic acid (HS5), and (9Z)-16-hydroxy-9,17-octadecadiene-12,14-diynoic acid (HS7) compound as an active ingredient for preventing and treating benign prostatic hyperplasia.

Furthermore, the present invention can provide a pharmaceutical composition including the above-described *Dendropanax morbifera* extract or compound derived, isolated and purified from the above-described *Dendropanax morbifera* extract as an active ingredient for preventing and treating prostate cancer.

The above-described compound of the present invention may be used in the form of salts, preferably in the form of salts that are pharmacologically acceptable. As the above-described salt, it is preferable to use acid addition salts that are formed by pharmacologically acceptable free acid, and as the above-described free acid, organic acids and inorganic acids may be used. The above-described organic acids include, but are not limited to, citric acids, acetic acids, lactic acids, tartaric acids, maleic acids, fumaric acids, formic acids, propionic acids, oxalic acids, trifluoroacetic acids, benzoic acids, gluconic acids, metasulfonic acids, glycolic acids, succinic acids, 4-toluenesulfonic acids, glutamic acids, and asparatic acids. In addition, the inorganic acids include, but are not limited to, hydrochloric acids, bromic acids, sulfuric acids, and phosphoric acids.

Moreover, besides the *Dendropanax morbifera* extract and the HS3, HS5, or HS7 compounds as an active ingredient, the pharmaceutical composition of the present invention may be prepared using pharmaceutically adequate and physiologically acceptable supplements, and as the above-described supplements, excipients, disintegrants, sweeteners, binding agents, coating agents, expansion agents, lubricants, modifiers, or flavoring agents may be used.

The above-described pharmaceutical composition may be preferably formulated by including more than one type of pharmaceutically acceptable carriers for administration in addition to the above-described active ingredients.

As possible formulation of the above-described pharmaceutical composition, there may be granules, powders, tablets, coated tablets, capsules, suppository, liquid formulation, syrups, juice, suspensions, emulsions, fluid infusion, and injectable liquid formulation, and it may be formulated as an intraurethral cream, rectal suppository or percutaneous formulation. For example, in order to formulate as tablets or capsules, the active ingredients may be combined with orally nontoxic and pharmaceutically acceptable inactive carriers such as ethanol, glycerol and water. In addition, if desired or necessary, adequate binding agents, lubricants, disintegrants and coloring agents may also be included in a mixture. The adequate binding agents include, but are not limited to, natural sugars such as starch, gelatin, glucose or β-lactose, natural and synthetic gums such as corn sweeteners, acacia, tragacanth or sodium olate, and sodium stearate, magnesium stearate, sodium benzoate, sodium acetate, and sodium chloride. The disintegrants include, but are not limited to, starch, methyl cellulose, agar, bentonite, and xantan gum. As pharmaceutically acceptable carriers that are appropriate for being sterilized and being used in vivo for composition in liquid solution, saline solution, sterilized water, Ringer's solution, buffered saline solution, albumin injection solution, dextrose solution, maltodextrin solution, glycerol, ethanol, and more than one ingredient among them may be mixed and used, and if necessary, other commonly used additives such as antioxidants, buffer solutions, and bacteriostatic agents may be added. Moreover, diluents, dispersing agents, surfactants, binding agents and lubricants may be additionally included to formulate as solution for injection including aqueous solution, suspension, and emulsion and pill, capsule, granule or tablets. Furthermore, as an appropriate method of the related art, it may be preferably formulated depending on each disease or ingredient by using the methods described in Remington's Pharmaceutical Science, Mack Publishing Company, Easton Pa.

In one exemplary embodiment of the present invention, the *Dendropanax morbifera* extract of the present invention may be included in the amount of 0.00001 to 30 wt % with respect to the total weight.

The composition of the present invention may also be used as functional food composition for preventing and relieving benign prostatic hyperplasia and prostate cancer, and besides having a *Dendropanax morbifera* extract as an active ingredient, as it is found for any other common food compositions, these food compositions may also include a number of flavoring agents or natural carbohydrates as additional ingredients.

As examples of the above-described natural carbohydrates, there may be monosaccharide, for example, glucose, fructose; disaccharide, for example, maltose, sucrose; polysaccharide, for example, common sugars such as dextrin and cyclodextrin, and sugar alcohols such as xylitol, sorbitol, and erythritol. As the above-described flavoring agents, natural flavoring agent (thaumatin), stevia extract (for example, rebaudioside A, glycyrrhizin) and synthetic flavoring agent (saccharin, aspartame) may be useful.

The food composition of the present invention may be formulated in the same manner as the above-described pharmaceutical composition, and may be used as a functional food or may be added to various foods. As the foods to which the composition of the present invention may be added, there are beverages, meat, chocolates, foods, snacks, pizza, instant noodles, other noodles, chewing gums, candies, ice creams, alcohol beverages, vitamin complexes and health supplemental foods.

In addition, besides *Dendropanax morbifera* extract, the active ingredient, the above-described food composition may include a number of nutritional supplements, vitamins, minerals (electrolytes), flavoring agents including synthetic and natural flavoring agents, coloring agents and enhancement agents (cheese and chocolate), pectic acids and salts thereof, alginic acids and salts thereof, organic acids, protective colloidal viscosity agents, pH adjusting agents, stabilizers, preservatives, glycerin, alcohols and carbonating agents used for carbonated drinks. In addition, the food composition of the present invention may include fruit juices used in production of natural fruit juice, fruit juice beverages, and vegetable beverages.

The *Dendropanax morbifera* extract, that is, the active ingredient of the present invention is a natural substance that has practically no toxicities and side effects, and therefore, it may be safely used for long term for preventing and relieving benign prostatic hyperplasia.

Therefore, the present invention provides a health functional food including a *Dendropanax morbifera* extract as an active ingredient for preventing and relieving benign prostatic hyperplasia and prostate cancer.

The health functional food of the present invention may be prepared and processed in the forms of tablets, capsules, powders, granules, liquid, and pills for the purpose of preventing and relieving of benign prostatic hyperplasia and prostate cancer.

The health functional food of the present invention refers to the food that is prepared and processed by using raw materials or ingredients with useful functionalities for human body pursuant to the article 6727 of the law for health functional foods, and refers to the act of eating for the purpose of regulating nutrition for structure of human body or its function or obtaining useful health effects such as physiological reactions.

The health functional food of the present invention may include some common food additives and regarding the adequacy of food additives, and unless other pertinent regulations are in effect, it is determined by standard and criteria for relevant product pursuant to the all-time general provisions and general test protocols of food additives approved by Korea Food & Drug Administration.

As the above-described food additives that are all-time listed, there may be for example, chemical composites such as ketones, glycine, calcium citrate, nicotinic acid, and cinamic acid; natural additives such as persimmon color, licorice extract, crystalline cellulose, Kaoliang color, and guar gum; mixed formulations such as sodium L-glutamic acid, alkali additives for noodles, preservatives, and tar color.

For example, the health functional foods in a tablet formulation may be prepared by performing the compression molding through adding modifiers after conducting the granulation of the mixture of the *Dendropanax morbifera* extract, that is, the active ingredient of the present invention, excipient, binding agent, disintegrant and other additives, or by performing directly the compression molding of the above-described mixture. Moreover, the above-described health functional food in tablet formulation may include corrigent, if necessary.

Among the health functional foods in a capsule formulation, the hard capsule formulation may be prepared by filling the mixture prepared by mixing a *Dendropanax morbifera* extract, that is, the active ingredient of the present invention, and the additives such as excipient, in the common hard capsules, and the soft capsule may be prepared by filling the mixture prepared by mixing the *Dendropanax morbifera* extract and additives such as excipient in the capsule materials such as gelatin. The above-described soft capsules may include plasticizers, coloring agents, and preservatives such as glycerin or sorbitol, if necessary.

The health functional foods in a pill formulation may be prepared by a previously known molding method using the mixture of *Dendropanax morbifera* extract, that is, the active ingredient of the present invention, excipient, binding agent, and disintegrant, and if necessary, they may be coated with white sugar or other coating agents, or the surface thereof may be coated with starch and talc.

The health functional foods in a granule formulation may be prepared in granular form by a previously known method with the mixture consisting of *Dendropanax morbifera* extract, that is, the active ingredient of the present invention, excipient, binding agent, and disintegrant, and if necessary, the fragrance ingredients and corrigents may be included.

The above-described health functional foods may be beverages, meat, chocolates, foods, snacks, pizza, instant noodles, other noodles, chewing gums, candies, ice creams, alcohol beverages, vitamin complexes and health supplemental foods.

Moreover, the present invention provides the prevention or treatment methods for benign prostatic hyperplasia including the administration of *Dendropanax morbifera* extract to mammals.

The term "mammal" used herein means a mammal that is subject of treatment, observation or experiment and preferably, it refers to human.

The term "therapeutically effective amount" used herein means the amount of active ingredient or pharmacological composition that induces biological or medical reactions in systems, animals or humans by investigators, veterinarians, physicians, or other clinical studies and it includes the amounts that induce relief for diseases or disorders to be treated. It is clear to ordinary skill in the related art that the therapeutically effective dose and dose frequency for the active ingredient of the present invention can be altered depending on the desired effects. Therefore, the optimum dose can be easily determined by ordinary skill in the related art and it can be regulated by a number of factors including the type of disease, severity of disease, the amount of active ingredient and other ingredients included in the composition, type of formulation, age of patient, weight, general health condition, gender, diet, administration time, route of administration, secretion rate of the composition, duration of therapy, and concomitant drugs. In terms of therapeutic methods of the present invention, for adults, it is preferable to administer 1 mg/kg to 250 mg/kg when the *Dendropanax morbifera* extract of the present invention or compound derived from the above-described extract is administered one to several times a day.

For therapeutic methods of the present invention, the *Dendropanax morbifera* extract or composition including the compounds of the present invention derived from the above-described extract can be administered in common fashion such as oral, rectal, intravenous, peritoneal, intramuscular, intrasternal, percutaneous, topical, intraocular or subcutaneous administration and moreover, it can be used as a medical agent prepared in intraurethral cream, rectal suppository or percutaneous formulation.

EXAMPLES

Hereinafter, the present invention will be described in more detail with reference to exemplary embodiments. Since these exemplary embodiments are only illustrating the present invention, it is apparent for one of ordinary skill in the related art that the scope of the present invention is not interpreted as being limited by these exemplary embodiments. Moreover, all of the experiments were performed more than 3 times and data was presented as mean±SE. Statistical significance was determined by Student's t test. $P<0.05$ was considered as statistically significant.

Example 1: Preparation of *Dendropanax morbifera* Leaf Extract (1) Preparation of Extract The leaves of *Dendropanax morbifera* were collected in Kogu farm located at Seongam-ri, Muan-gun (eup), Republic of Korea. The collected *Dendropanax morbifera* leaves were dried in the shade at room temperature.

The dried leaves were extracted 3 times with methanol at room temperature. The methanol extracts described above were filtered through Whatman No. 1 filter paper, and the above-described combined methanol extracts were concentrated in vacuum using rotary evaporator. The methanol extracts were suspended in water and then fractionated according to the polarity in hexane, diethyl ether, ethyl acetate, n-butanol and water. Each of the extracts was concentrated using rotary evaporator. This process is illustrated in FIG. 1.

(2) Fractionation and Separation Process

Using a gradient solvent system [$CHCl_3$ (0.1% HCOOH) 100% through $CHCl_3$ (0.1% HCOOH)-MeOH (0.1% HCOOH)/55:45 for 120 min], 10 fractions were obtained (DEE01 to DEE10) by conducting the activity-guided fractionation of hexane extract under 254 and 280 nm with an Isolera Flash Purification system (BIOTAGE, Sweden). Each of the fractions was monitored using HPLC in gradient MeCN—$H_2O$ (0.1% HCOOH) solvent system, and each of the compounds was detected.

Furthermore, under UV light (254 nm), the spots were detected by a thin layer chromatography, or vanillin-$H_2SO_4$ were sprayed, and subsequently, heated at 110° C.

Using a SunFire™ Prep C18 (10⬛ 250 mm, and 19⬛ 150 mm, 5 µm) column with a MeCN/$H_2O$ gradient solvent system including 0.1% formic acid (30:70→100% MeCN), repetitive semi-preparative HPLC experiments were conducted for 40 minutes, and the compounds as major ingredients were finally isolated from these fractions.

(3) Results

The yields of *Dendropanax morbifera* extract depending on extraction solvent are listed in Table 1.

TABLE 1

The yields of *Dendropanax morbifera* extract depending on extraction solvent

| Solvent | Final product (g) | Yield (%) |
| --- | --- | --- |
| Methanol | 230.1 | 13.6 |
| n-hexane | 34.6 | 2.1 |
| Ethyl acetate | 31.0 | 1.9 |
| n-butanol | 46.6 | 2.8 |
| Water | 98.4 | 5.8 |

As a result, the yield of methanol extract was the highest, whereas the yield of ethyl acetate extract was somewhat low.

Example 2: Analysis of Cytotoxicity and Anti-Androgen Activity of *Dendropanax morbifera* Leaf Extract The inventors of the present invention conducted the experiments as follow in order to investigate whether or not the *Dendropanax morbifera* leaf extract of the present invention has stability in cells and anti-androgen activity. First of all, for cytotoxicity experiment, the LNCaP•FGC (androgen-dependent prostate cancer) cells were cultured in RPMI medium and 5% $CO_2$ humidified incubator at 37° C., and the culture media used were supplemented with 10% heat-inactivated FBS and 100 µg/mL penicillin. The cell viability assessment was conducted by a MTT assay (Mosmann, 1983), in which the LNCaP•FGC cells (4⬛ $10^4$/mL) were seeded per 90 µL of DMEM medium on 96-well plate. After overnight culture, the *Dendropanax morbifera* extract was treated for 72 hours and cultured in 10 µL of MTT (5 mg/mL stock solution) for 4 hours. Then, the medium was removed and formazan was dissolved by adding 150 μL of DMSO. Using an ELISA microplate reader (PerkinElmer, California, USA), absorbance at 540 nm was measured. The results are listed in the following Table 2 and illustrated in FIG. 2.

For the analysis of anti-androgen activity, the LNCaP•FGC cells, an androgen-dependent prostate cancer cell line, were used and the level of mRNA of PSA (Prostate specific antigen), which is one of the AR target genes, in prostate cancer was measured.

TABLE 2

Cytotoxicity test of LNCaP•FGC depending on extraction solvent used for *Dendropanax morbifera*

| Solvent | $IC_{50}$ for LNCaPFGC cells (ug/mL) |
|---|---|
| Methanol | 152 |
| n-hexane | 169 |
| Ethyl acetate | 88.3 |
| n-butanol | 562 |
| Water | >800 |

Figure 2:
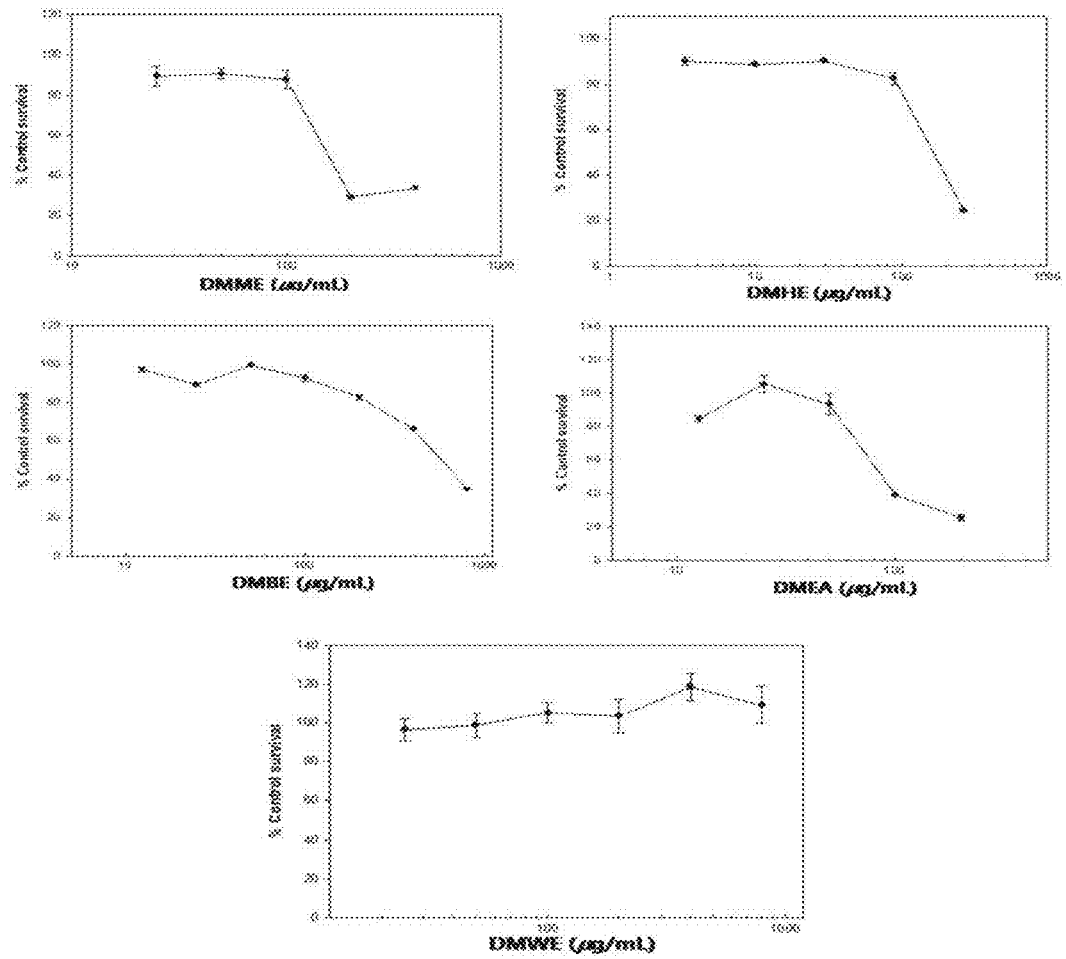
FIG. 2 is a graph illustrating the cytotoxicity assessment of *Dendrapanax morbifera* extract in cells by MTT assay.

As illustrated in FIG. 2 and listed in table 2 as described above, the $IC_{50}$ of *Dendropanax morbifera* hexane, ethyl acetate, methanol and water extracts are 88 μg/mL to higher than 800 μg/mL in LNCaP•FGC cells, and thus, it can be confirmed that the *Dendropanax morbifera* extract of the present invention is not lethal to cell viability, and not cytotoxic accordingly.

Example 3: Effect of Androgen Receptor Signaling Inhibition

Figure 3:
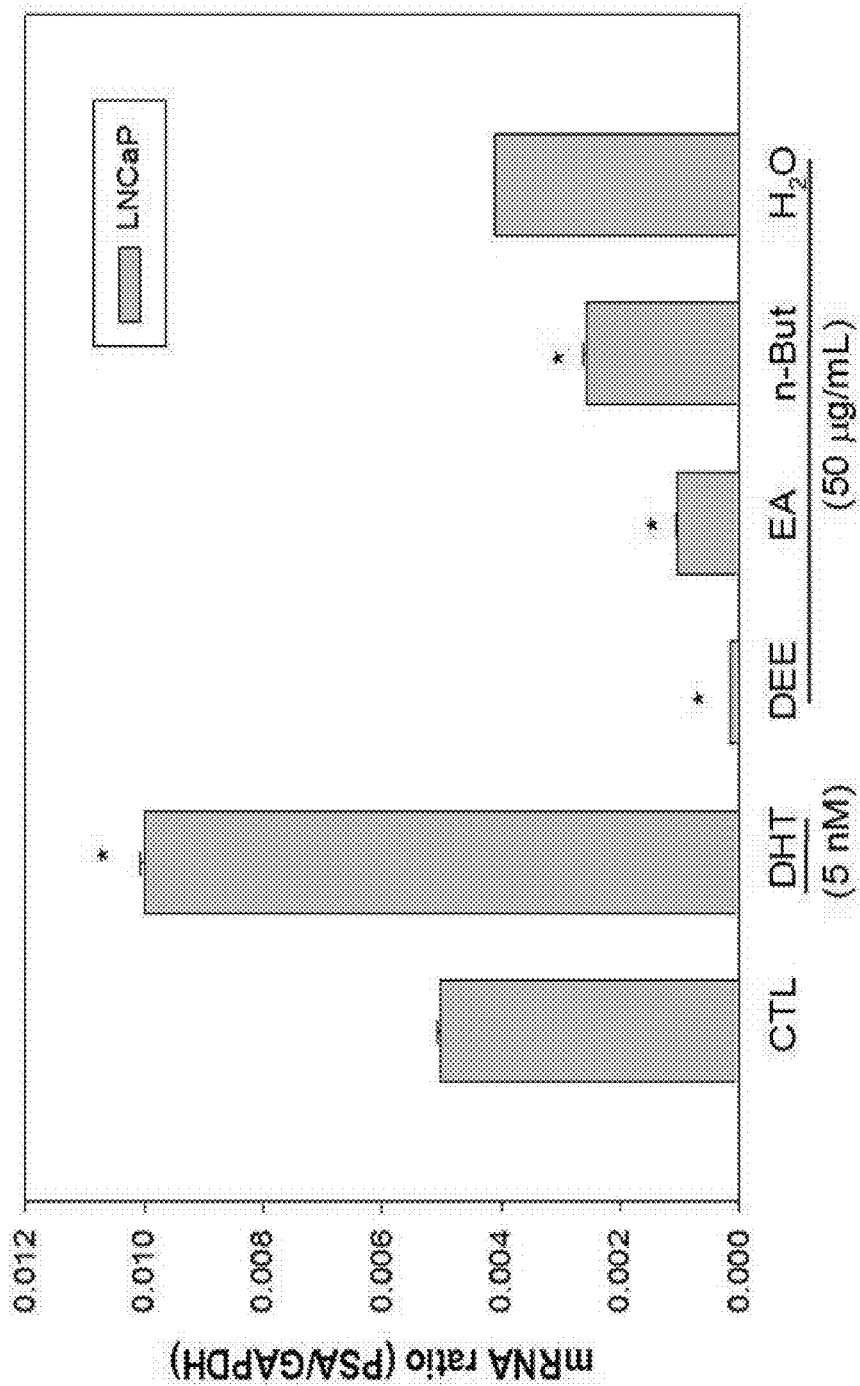
FIG. 3 is a graph illustrating the effects of *Dendrapanax morbifera* extract on the mRNA expression of PSA (prostate specific antigen) in LNCaP•FGC cells.
Figure 4:
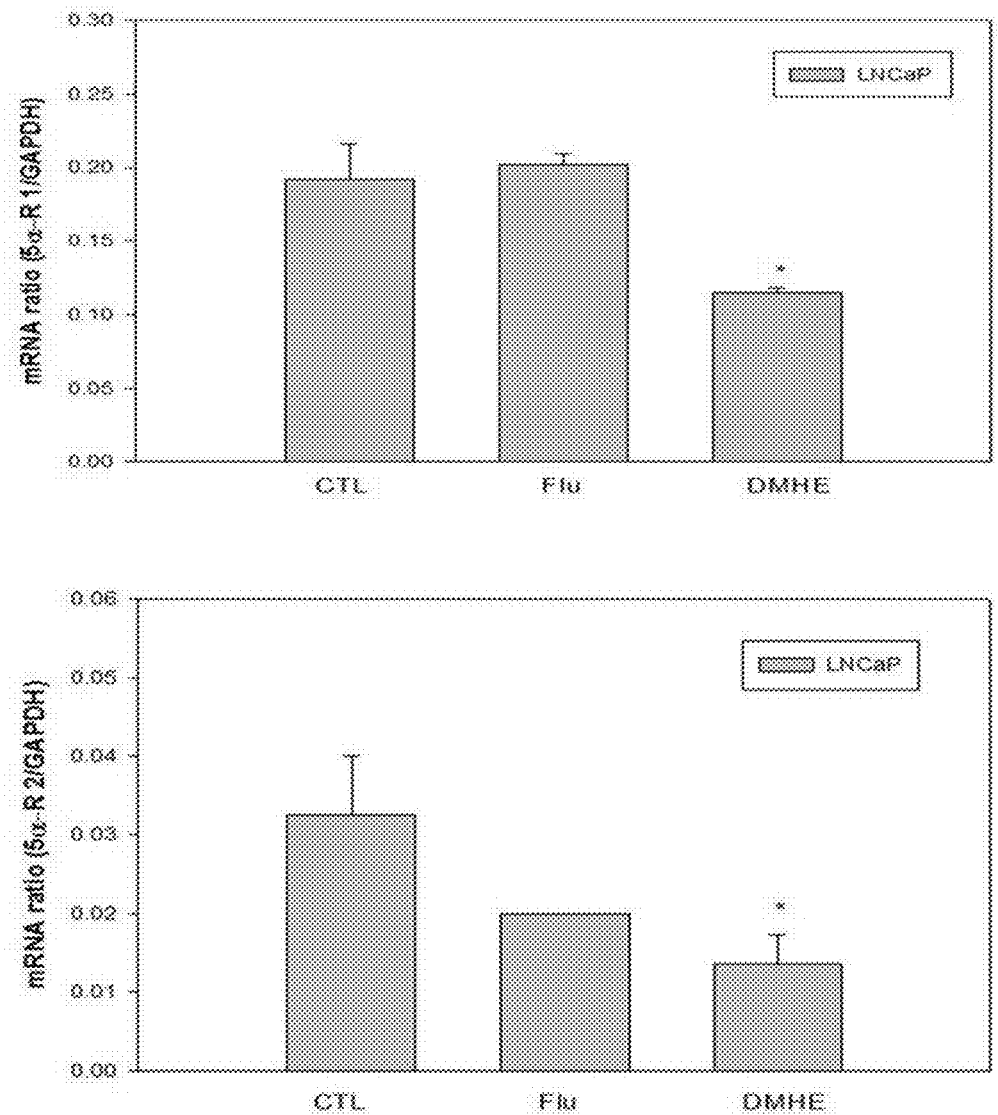
FIG. 4 is a graph illustrating the effects of *Dendrapanax morbifera* extract on the mRNA expression of 5α-R 1/2 in LNCaP•FGC cells.
Figure 5:
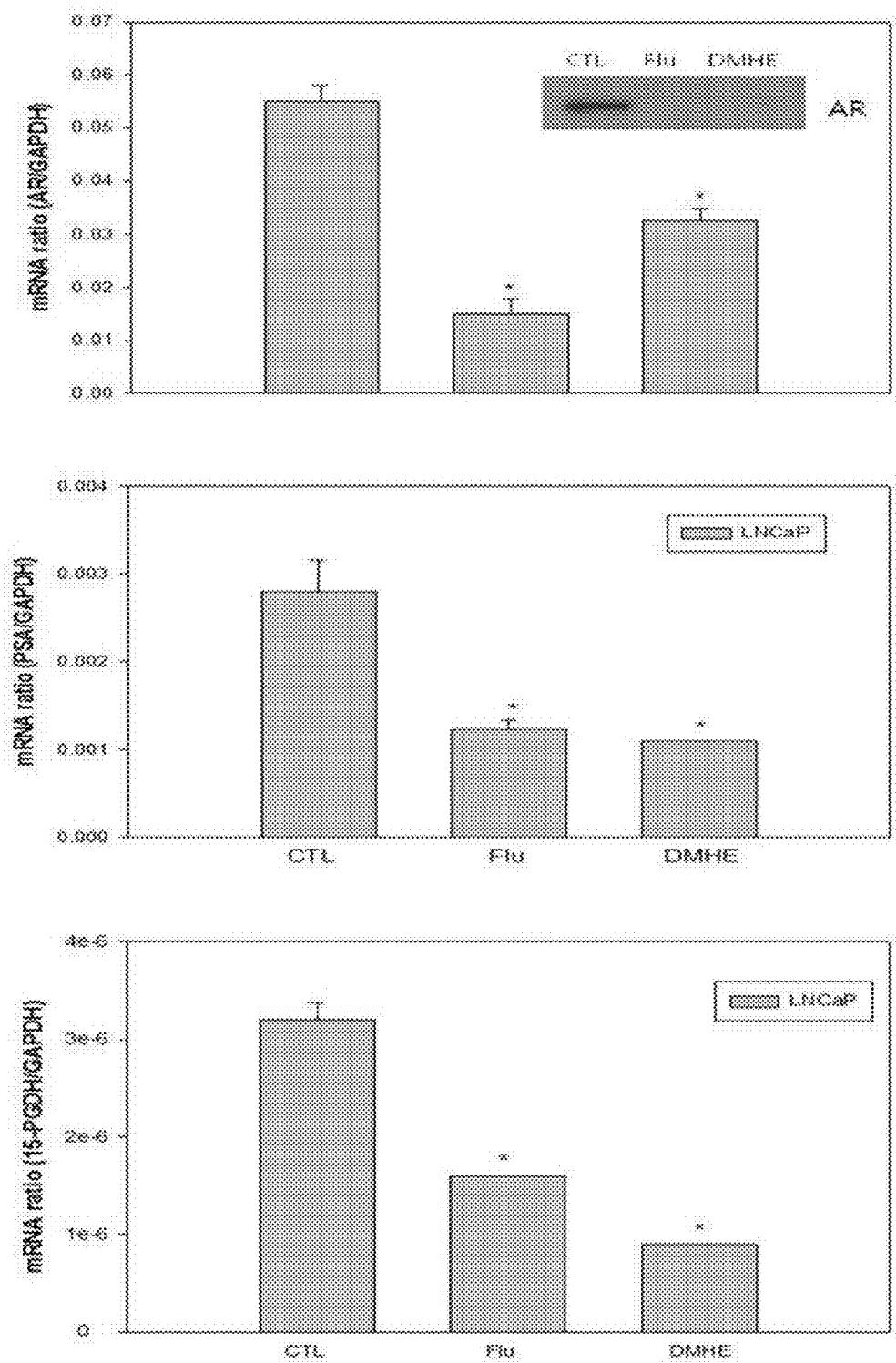
FIG. 5 is a graph illustrating the effects on the mRNA expression of DMHE, AR of flutamide, 15-hydroxyprostaglandin dehydrogenase (15-PGDH) and PSA in LNCaP•FGC cells.
Figure 6:
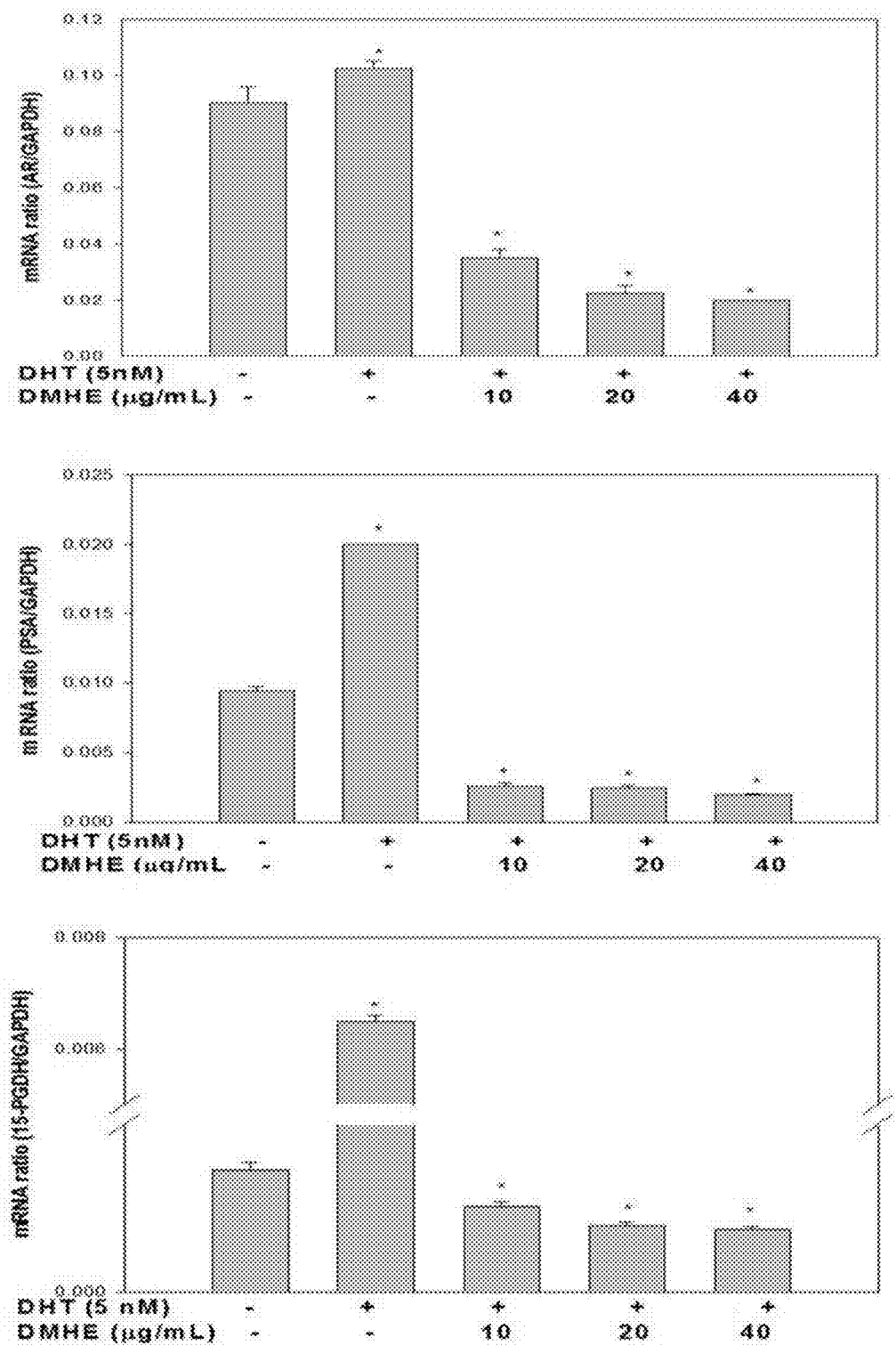
FIG. 6 is a graph illustrating the concentration-dependent effect of DMHE on over-expression of the mRNAs of AR, 15-PGDH and PSA, which are the target genes induced by DHT in LNCaP•FGC cells.
Figure 7:
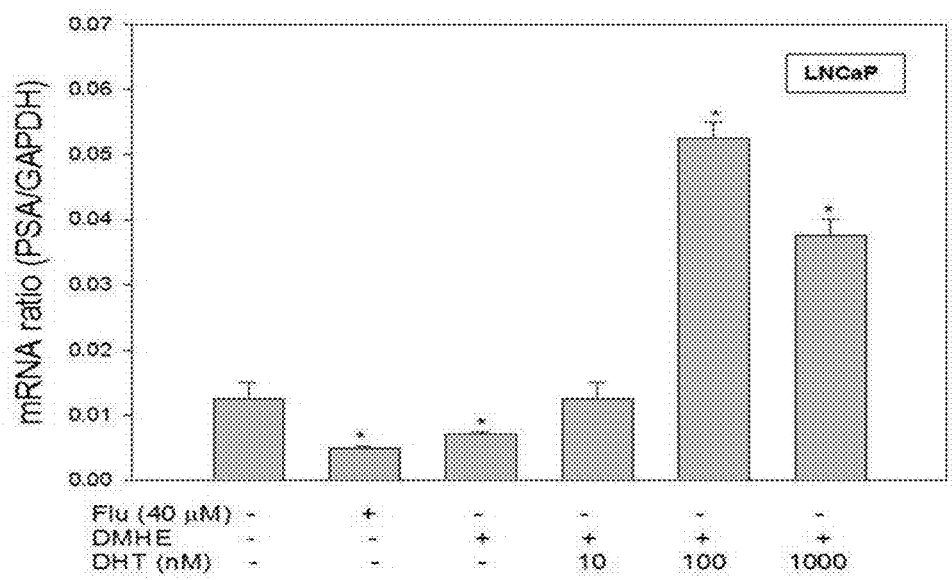
FIG. 7 is a graph illustrates that mRNA expression of PSA, the target gene of AR, inhibited by DMHE is recovered under high concentration of DHT, and this illustrates that AR is competitively inhibited by DHT and DMHE.

Moreover, from the analysis of effect on the activity of anti-androgen using a LNCaP•FGC prostate cancer cell line, an androgen-dependent cell, it was determined that the *Dendropanax morbifera* extract of the present invention inhibited DHT-induced expression of PSA mRNA and the degree of inhibition was determined to be in the order of n-Hex, EA, n-But and $H_2O$ extract (see FIG. 3), and DMHE, which is not a flutamide, reduced target genes including the expression of PSA and 15-PGDH in concentration dependent fashion by reducing 5αR-I/2 enzyme during the synthesis of DHT (see FIGS. 4 and 5). This was inhibited by addition of large amount of DHT, and these results indicate that the anti-androgen activity of DMHE originates from competitive mechanism with DHT in AR (see FIG. 7). Moreover, down-regulated gene expression of AR by DMHE was also observed in the cells treated with flutamide (see FIG. 5).

The anti-androgen effect of *Dendropanax morbifera* extract through a LNCaP•FGC prostate cancer cell line was identified once more by conducting the experiments as follow. In other words, primary Human Follicle Dermal Papilla Cells (HFDPC) (Cat. No. C-12071, PromoCell) were used in studying AR signaling as these cells have an androgen receptor (AR). HFDPC were purchased from PromoCell (Heidelberg, Germany) and they are positively stained in alkaline phosphatase. All primary HFDPC used herein underwent 34 passages and cultured by using Follicle Dermal Papilla Cell growth medium (C-26501, PromoCell, Germany) in 5% $CO_2$ humidified incubator at 37° C. The cultured HFDPC (5■ $10^5$/6 well) were vertically separated and after cells were attached, the DMHE of the present invention was treated for 24 hours. Later, its effects on the mRNA expressions of 15-PGDH, which is an intracellular target gene of AR, 5αR-1/2, which involve in converting testosterone to DHT and thereby amplifying its sensitivity to AR, and AR were investigated. As a result, the *Dendropanax morbifera* extract of the present invention was determined to be capable of inhibiting the expressions of 5αR-1, 5αR-2, AR, and 15-PGDH (FIGS. 18 to 21).

From these results, the inventors of the present invention identified that the *Dendropanax morbifera* extract of the present invention was a substance with an outstanding effect capable of inhibiting the mechanism by which benign prostatic hyperplasia occurs and can be used for treating benign prostatic hyperplasia.

Example 4: Analysis of Benign Prostatic Hyperplasia Treating Effect of *Dendropanax morbifera* Extract Through In Vivo Experiment The inventors previously identified the benign prostatic hyperplasia treating effect of *Dendropanax morbifera* extract through in vivo experiment and furthermore, they prepared an animal model with benign prostatic hyperplasia, in which they identified the benign prostatic hyperplasia treating effect of *Dendropanax morbifera* extract through experiments described below.

First of all, the animals used for experiments were 11-week old male Sprague Dawley mice, which were purchased from Damul Science Co. (Daejeon, Republic of Korea). They were provided with hard food and water frequently and were used in experiments after a week of adaptation period for laboratory environment and the animal experiments conducted herein were approved by Chonnam National University animal experiment ethics committee (IRB) (CNU IACUC-YB-R-2012-9).

<4-1> Preparation of Mouse Animal Model with Benign Prostatic Hyperplasia

The male Sprague Dawley mice were divided into the groups such as vehicle control group (V-CTL) that is an experimental group, the group administered with testosterone only (TP-CTL), the group administered with finasteride as positive control for testosterone (TP+FS) and the groups administered with *Dendropanax morbifera* (TP+DMH), and for each group, n was equal to 4 and overall experimental procedure is as illustrated in Table 3. For 2 weeks, testosterone was administered subcutaneously to induce prostatic hyperplasia and 2 weeks later, it was confirmed whether prostatic hyperplasia was sufficiently induced through removal and then, monitored the inhibition of benign prostatic hyperplasia by administering the *Dendropanax morbifera* extract of the present invention everyday while maintaining prostatic hyperplasia with continuous injection of testosterone. As a positive control group, the finasteride (2 mg/kg/day) was used and the *Dendropanax morbifera* extract was administered for 2 groups (0.5 and 2 mg/kg). 3 weeks after the drug administration, the mice were sacrificed and the results were observed.

TABLE 3

Overall experimental schedule of animal model with benign prostatic hyperplasia

| Group | 0 day | 14 day | 35 day |
|---|---|---|---|
| V-CTL | Corn oil (s.c.)/day | Corn oil (s.c.)/day | + CMC (p.o.)/day |
| TP-CTL (3 mg/kg) | TP (s.c.)/day | TP (s.c.)/ /day | + CMC (p.o.)/day |

TABLE 3-continued

Overall experimental schedule of animal model with benign prostatic hyperplasia

| Group | 0 day | 14 day | 35 day |
|---|---|---|---|
| TP + PS (2 mg/kg) | TP (s.c.)/day | TP (s.c.)/day + Fina (p.o., 2 g/kg)/day | |
| TP + DMHE (0.5 mg/kg) | TP (s.c.)/day | TP (s.c.)/day + DMH (p.o., 0.5 mg/kg)/day | |
| TP + DMHE (2 mg/kg) | TP (s.c.)/day | TP (s.c.)/day + DMH (p.o., 2 mg/kg)/day | |

V, vehicle administration group; CTL, control group; TP, testosterone-propionate administration group; FS, finasteride administration group; DMHE, *Dendropanax morbifera* hexane extracts administration group; CMC, carboxymethylcellulose administration group.

Figure 8:
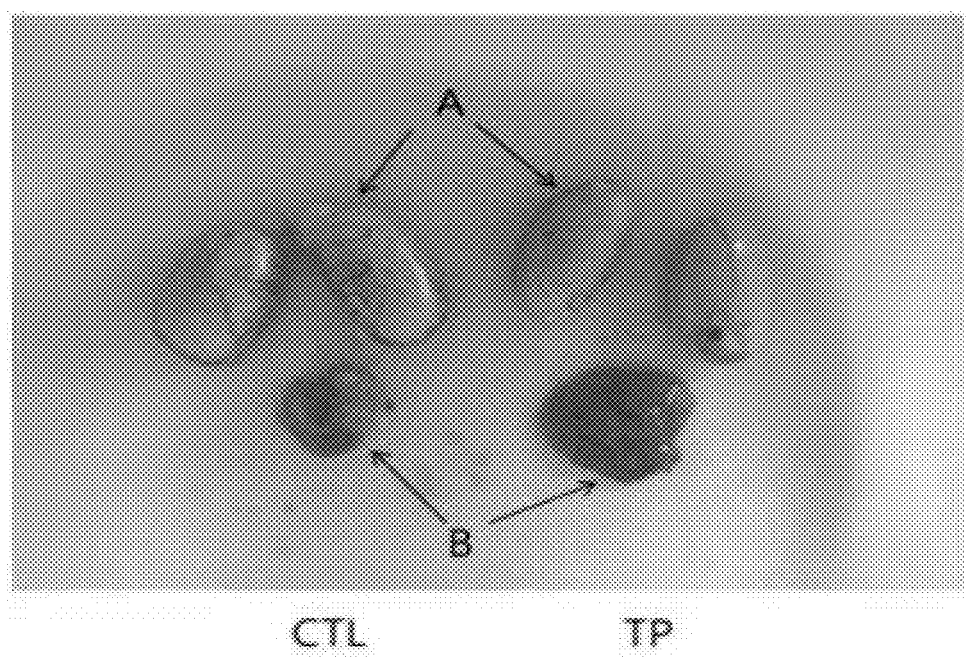
FIG. 8 is a photograph illustrating the degree of benign prostatic hyperplasia observed with an unaided eye in benign prostatic hyperplasia animal models prepared in one exemplary embodiment of the present invention.
Figure 9:
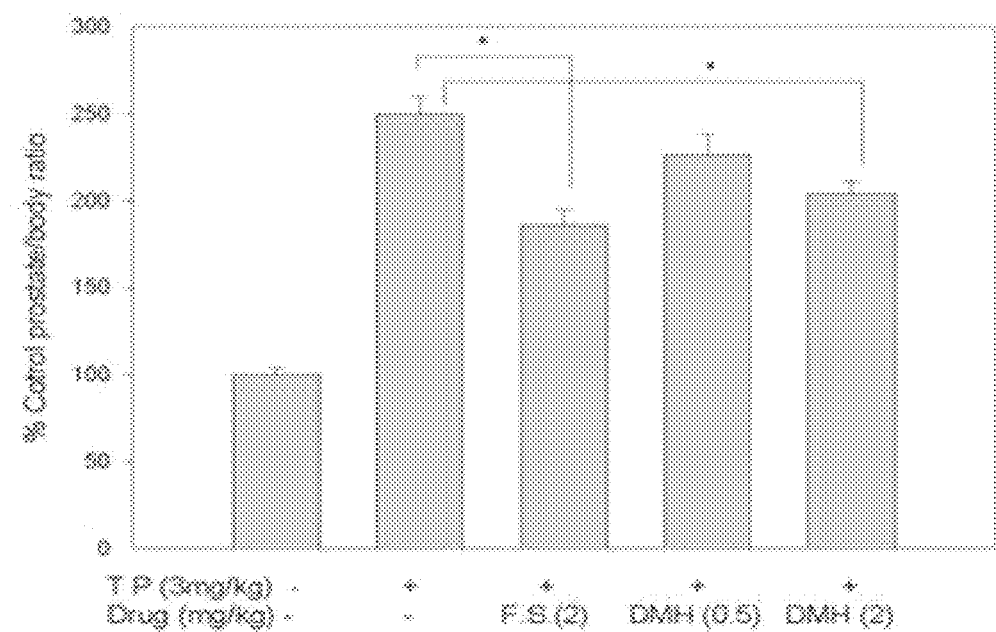
FIG. 9 illustrates the change in size of prostate of mouse model with benign prostatic hyperplasia measured upon the treatment of *Dendropanax morbifera* extract of the present invention.

For 2 weeks, TP was administered subcutaneously everyday in order to induce prostatic hyperplasia and 2 weeks later, it was identified whether the prostatic hyperplasia was properly induced by dissecting the vehicle treated control group and TP treated control group and as a result illustrated in FIG. 8, the size of prostate was identified to be enlarged to 189% of control group.

<4-2> Analysis of Change in the Size of Prostate and Ratio of Prostate to Body Weight From the previously described experiment schedule, blood and prostate were collected after measuring the body weight and sacrificing on the day after the last day of administration. The weight of removed prostate was measured after removing the surrounding fats and foreign substances and the weight ratio of prostate to body was calculated by the following equation and the result is listed in Table 4.

Prostate weight (g)/body weight (g) × 100

TABLE 4

Effect of drug administration on prostate in benign prostatic hyperplasia model

| Group | Weight of prostate | prostate %/body weight (w/w) | % V-CTL ratio | % TP-CTL ratio |
|---|---|---|---|---|
| V-CTL | 0.55 ± 0.04 | 0.12 ± 0.008 | 100.0 ± 6.2 | |
| TP-CTL | 1.22 ± 0.12 | 0.30 ± 0.019 | 249.9 ± 19.4 | 100.0 ± 7.8 |
| TP + FS (2 mg/kg) | 0.95 ± 0.12 | *0.22 ± 0.018 | 185.7 ± 15.1 | 74.3 ± 3.2 |
| TP + DMHE (0.5 mg/kg) | 1.14 ± 0.06 | 0.27 ± 0.021 | 226.6 ± 17.6 | 90.7 ± 7.0 |
| TP + DMHE (2 mg/kg) | 1.03 ± 0.07 | *0.24 ± 0.019 | 203.9 ± 15.9 | 81.6 ± 6.3 |

V, vehicle administration group;
CTL, control group;
TP, testosterone-propionate administration group;
FS, finasteride administration group;
DMHE, *Dendropanax morbifera* hexane extracts administration group.
P < 0.05.

As a result of analysis, when TP was treated for 5 weeks, the point at which experiments are completed, the prostate size of TP-CTL increased up to 249% of V-CTL. When the weight of enlarged prostate decreased by drug treatment for group treated with FS (3 mg/kg/day) and group treated with the *Dendropanax morbifera* extract (2 mg/kg) were compared with those of TP-CTL, statistically significant difference was observed (P<0.05). When the weight ratio was compared to that of TP-CTL, it showed 74.3% decrease in size for group treated with FS, and 90.7% and 81.5% decrease in sizes for groups treated with 0.5 mg/Kg and 2 mg/Kg of the *Dendropanax morbifera* extract, respectively.

<4-3> Analysis of PSA (Prostate Specific Antigen) Content in Blood

From the sacrificed mouse in the above example, the plasma was isolated from blood and the content of PSA was determined. PSA measurement was conducted using ELISA (MyBiosource, Arizona, USA) according to the manufacturer's experimental protocol and presented as pg/mL content.

TABLE 5

Effect of DMHE on PSA concentration in blood of mouse with benign prostatic hyperplasia

| Sample | PSA (pg/mL) | % Vehicle control | % TP control |
|---|---|---|---|
| TP (3 mg/kg) | 931.3 ± 166.6 | 54.2 ± 9.8 | 100 |
| TP + FS (2 mg/kg) | *323.0 ± 85.0 | 18.7 ± 5.0 | 34.6 |
| TP + DMHE (0.5 mg/kg) | 818.0 ± 220.0 | 47.7 ± 12.8 | 87.9 |
| TP + DMHE (2 mg/kg) | *404.3 ± 353.3 | 23.5 ± 20.6 | 43.4 |

TP: Testosterone propionate,
FS: Finasteride,
DMHE: *D. morbifera* hexane extract.
P < 0.05

Figure 11:
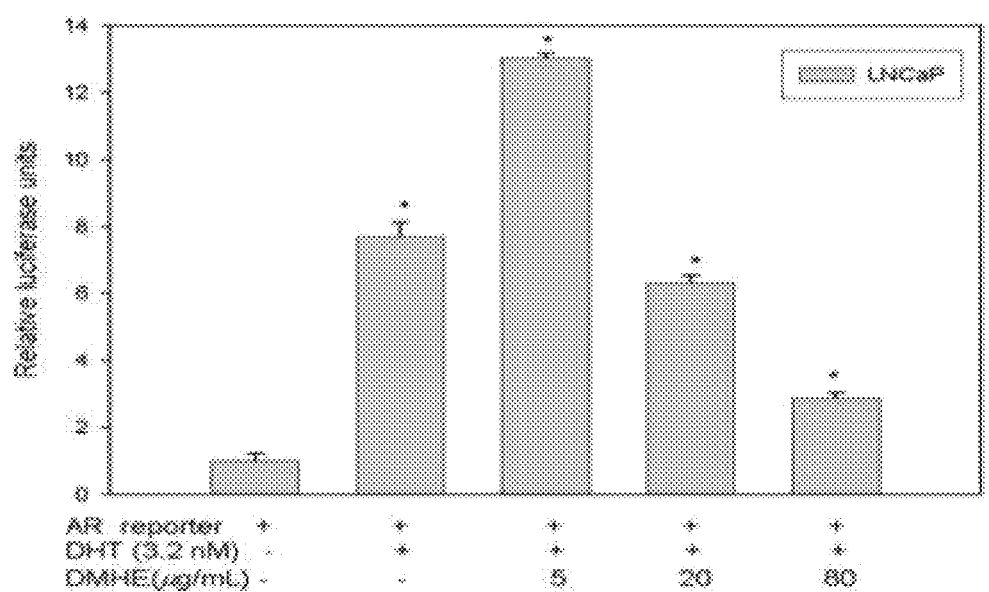
FIG. 11 illustrates the result of analysis, in which the concentration of blood stream PSA of the above-described mouse model with benign prostatic hyperplasia was measured upon the treatment of *Dendropanax morbifera* extract of the present invention.

As a result illustrated in Table 5 and FIG. 11 above, the PSA concentration of group treated with the *Dendropanax morbifera* hexane extract (DMHE) was 87.9% for DMHE (0.5 mg/kg) and 43.4% for DMHE (2 mg/kg), respectively with respect to that of group treated only with TP (3 mg/kg), and these results represent that the treatment effect is remarkably huge, given that the PSA concentration of positive control group treated with FS (finasteride) (2 mg/kg) that is used as benign prostatic hyperplasia treatment was 34.6%.

Example 5: Analysis of Effect of *Dendropanax morbifera* Extract on the Transcriptional Activity of Androgen Receptor A reporter gene assay was conducted in order to investigate whether or not the *Dendropanax morbifera* extract has direct effect on the transcriptional activity of an androgen receptor (AR). The AR reporter gene assay was conducted using a Cignal™ Reporter assay kit (Qiagen, CA, USA). The transfection conditions were established using the compound containing a GFP construct and using a Polyplus transfection reagent (Polyplus, New York, USA) in androgen-dependent LNCaP•FGC cells, and then it was confirmed whether or not the reporter gene is properly activated before the experiments were conducted. The LNCaP•FGC cells were aliquoted into 25🬋 10⁴/12 well, and after the transfection of each of AR reporter (100 ng) and negative control group (100 ng), the medium was replaced with an assay medium (Opti-MEM+1% FBS+0.1 mM NEAA) when 16 hours were passed, and then 24 hours after the transfection, the DHT was treated in order to measure the agonistic activity. Moreover, in order to measure the antagonistic activities of *Dendropanax morbifera* extract, the cells were collected after being treated with DHT and also DMHE with multiple concentrations and cultured for 18 hours. The collected cells were rinsed with PBS (pH 7.4) buffer three times and lysed using passive lysis buffer (Promega, Madison, Wis., USA). The cell lysates were immediately analyzed using a 96 well plate luminometer (Berthold Detection system, Pforzheim, Germany). The amounts of firefly luciferase and Renilla luciferase were analyzed using a Dual-luciferase reporter assay system kit (Promega, Madison, Wis., USA). The luciferase values of each experimental group were normalized with respect to the activity of Renilla luciferase and represented as fold value, which represents the relative transcriptional activity.

Figure 10:
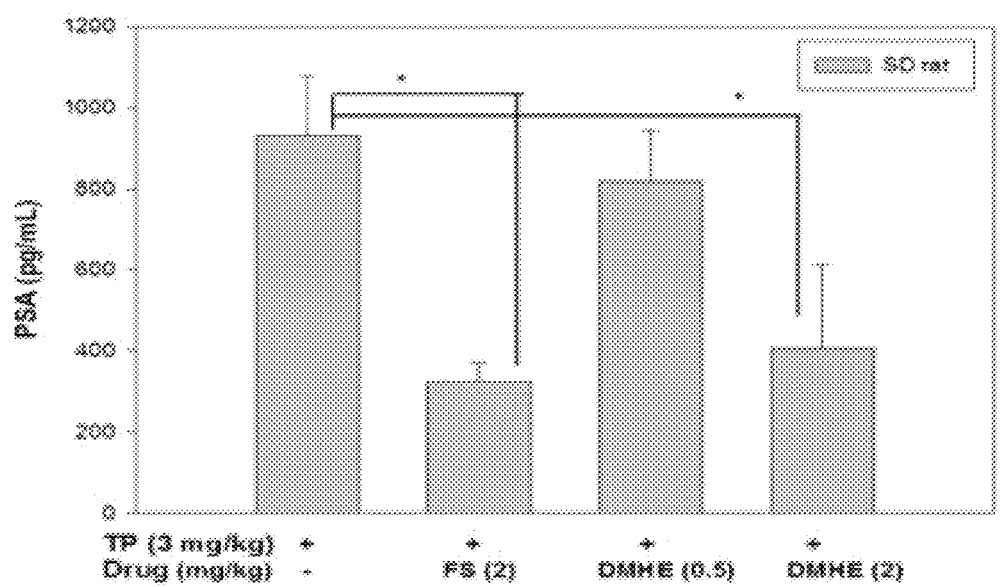
FIG. 10 illustrates the results of luciferase assay, in which the transcriptional activities of androgen receptor were analyzed in LNCaP•FGC cells upon the treatment of *Dendropanax morbifera* extract of the present invention.

As a result illustrated in FIG. 10, it was identified that the transcriptional activity of AR reporter gene activated by DHT is inhibited by DMHE in concentration dependent fashion. Therefore, it was confirmed once again that the decrease in mRNA of PSA by *Dendropanax morbifera* extract, which is the target gene of LNCaP•FGC cell, is the inhibition by antagonistic effect of AR gene.

Example 6: Isolation and Identification of Compounds that have Treatment Effect for Benign Prostatic Hyperplasia from *Dendropanax morbifera* Extract The present inventors learned that *Dendropanax morbifera* extract has treatment effect for benign prostatic hyperplasia through the above-described examples and following experiments were conducted in order to identify the active ingredient capable of treating benign prostatic hyperplasia from the above-described *Dendropanax morbifera* extract.

Figure 12:
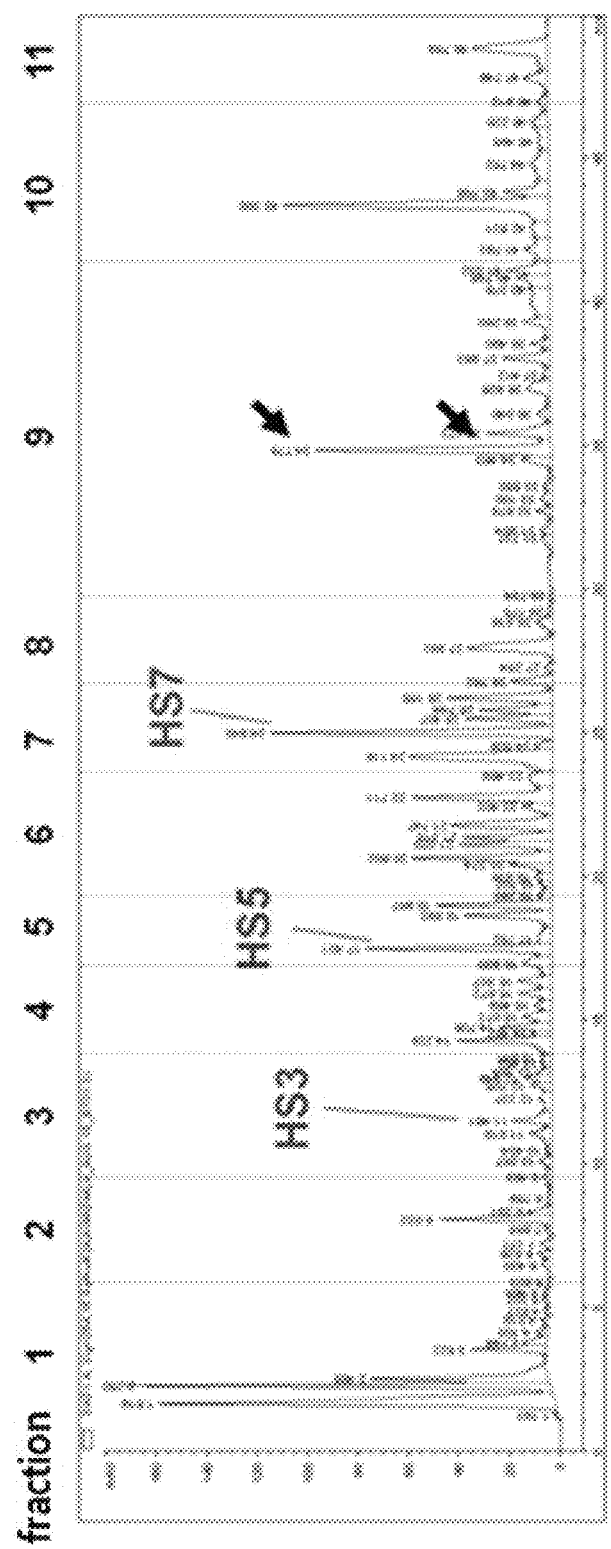
FIG. 12 is a chromatogram illustrating the isolation of a single compound through HPLC chromatography analysis of *Dendropanax morbifera* hexane extract in one exemplary embodiment of the present invention.

That is, as a result of the preliminary investigation, in which the chemical structures of active ingredients of the above-described *Dendropanax morbifera* extract with anti-androgen activity were analyzed using a HPLC under the condition of a gradient solvent system [MeCN—H$_2$O (0.1% HCOOH), 30:70→100:0 (40 min), 100% MeCN (10 min), PDA detector], it was revealed that polyacetylene substances prevail (see FIG. 12). Then, the 11 fractions of hexane extract were obtained by performing a reversed phase medium chromatography with a gradient solvent [MeCN—H$_2$O (0.1% HCOOH), 30:70 (5 min), 30:70→67:33 (80 min), 67:33→100% MeCN (5 min), 100% MeCN (30 min)] for part of the above-described *Dendropanax morbifera* extract (4.79 g) and by performing isolation and purification for fraction 3 (112.3 mg), fraction 5 (117.4 mg), and fraction 7 (120.2 mg) using a HPLC, single substances, HS3 (2.9 mg), HS5 (8.4 mg) and HS7 (30.0 mg) were monitored, detected and isolated in MeCN—H$_2$O (0.1% HCOOH) gradient solvent system.

Later, as a result of chemical structure analysis for each single substance through NMR, UV, and MS analysis, three substances were identified to be a 9,16S-dihydroxy-10,17-octadecadiene-12,14-diynoic acid (HS3), 9,16R-dihydroxy-10,17-octadecadiene-12,14-diynoic acid (HS5), and (9Z)-16-hydroxy-9,17-octadecadiene-12,14-diynoic acid (HS7), which are all diacetylene substance.

Figure 13:
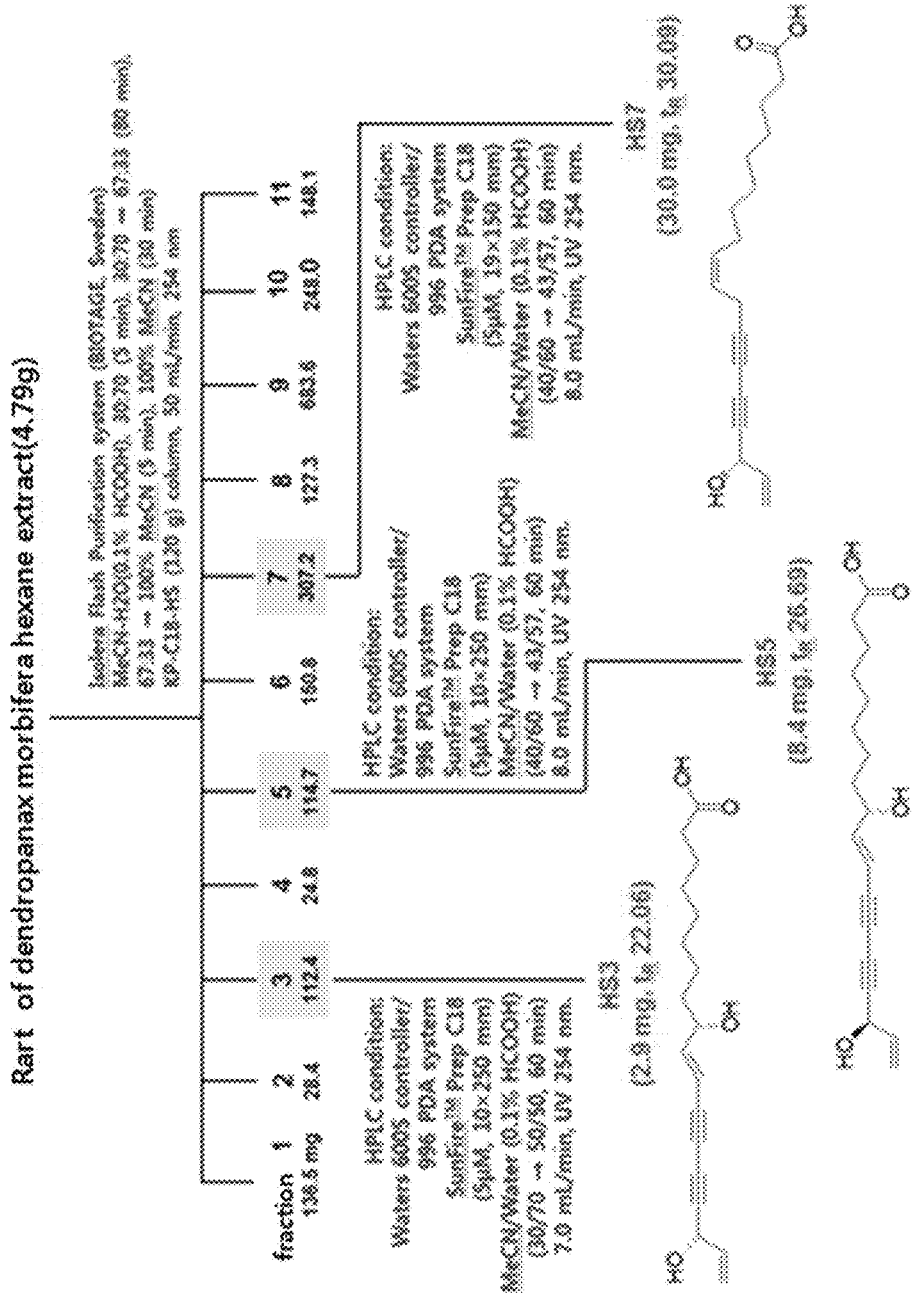
FIG. 13 is a schematic diagram illustrating the process of isolating and purifying 3 types of single compounds that have benign prostatic hyperplasia treatment effect from *Dendropanax morbifera* hexane extract of the present invention.

The purification procedure and chemical structure of each 3 compound isolated and purified by the above-described methods of the present invention were illustrated in FIG. 13.

Example 7: Identification of Effect of Compounds Isolated from *Dendropanax morbifera* Hexane Extract on Treating Benign Prostatic Hyperplasia In order to identify whether or not the 3 compounds isolated and identified from Example 6 have treatment effect for benign prostatic hyperplasia, and in order to investigate the effect on AR signaling, the effects on the mRNA expression of PSA, 15-PGDH and 5αR-1/-2 were investigated when the above-described compounds were treated.

In the analysis, the levels of mRNA expressions of the above-described genes were measured after treating LNCaP•FGC cells with the *Dendropanax morbifera* solvent extract of the present invention, 3 single compounds isolated and identified from the above-described extract, and flutamide (40 μM) as a positive control group for 48 hours, respectively.

<7-1> Analysis Result of the Level of PSA mRNA Expression

Figure 14:
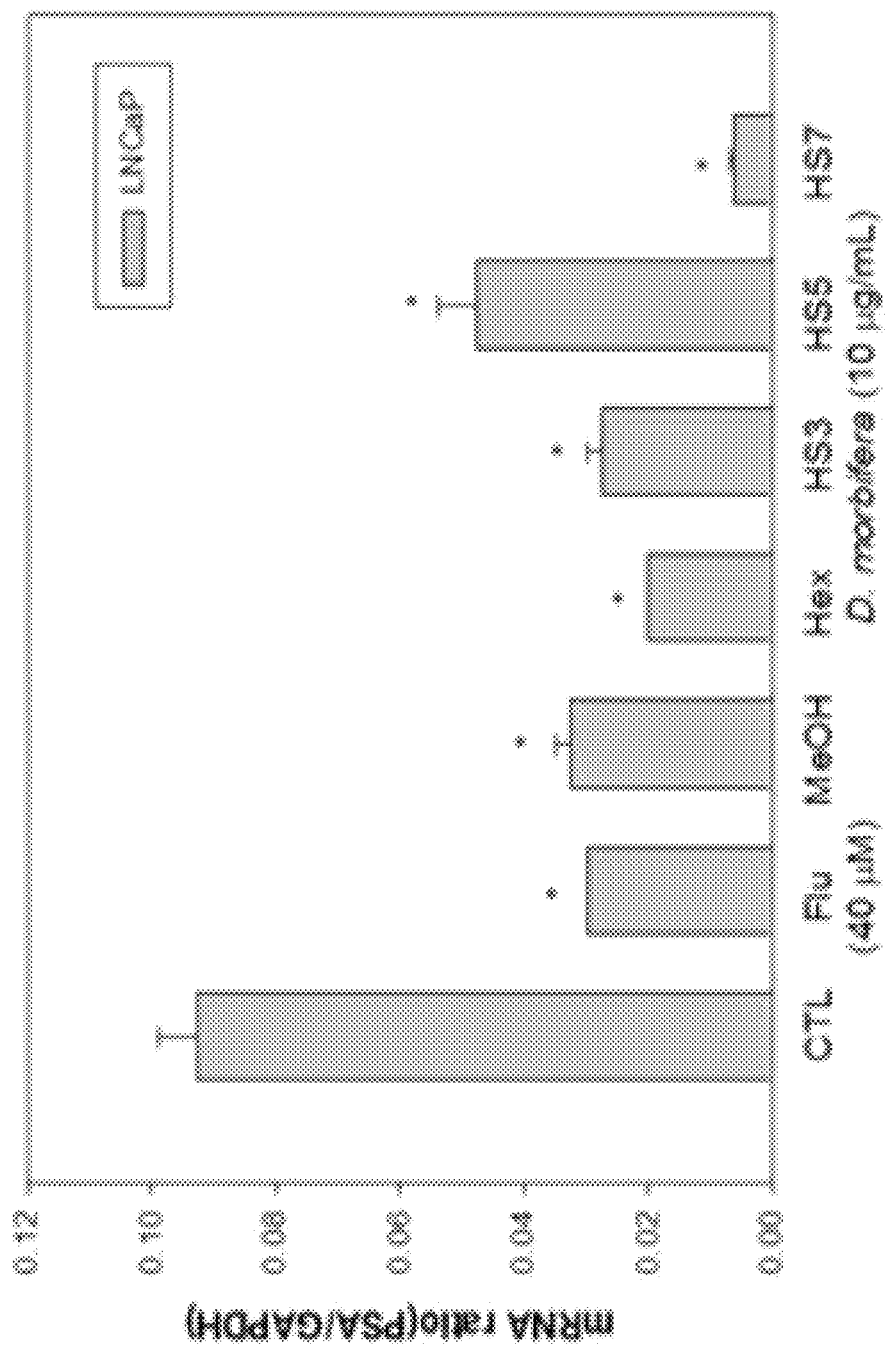
FIG. 14 illustrates the result of analysis, in which the effects of *Dendropanax morbifera* hexane extract of the present invention and 3 single compounds derived from the above-described extract on the expression of PSA mRNA in prostate cancer cell line (LNCaP•FGC) were analyzed.
Figure 15:
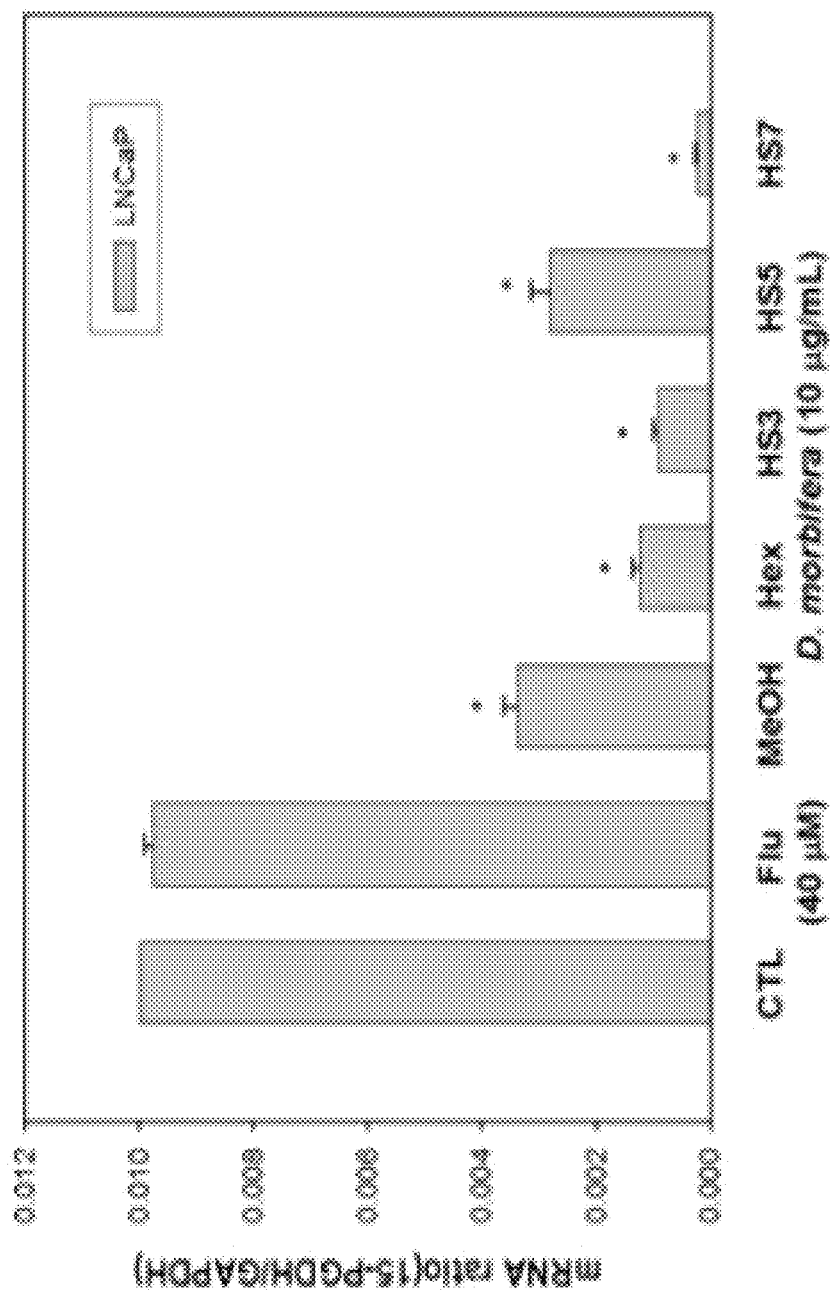
FIG. 15 illustrates the result of analysis, in which the effects of *Dendropanax morbifera* hexane extract of the present invention and 3 single compounds derived from the above-described extract on the expression of 15-PGDH mRNA in prostate cancer cell line (LNCaP•FGC) were analyzed.

As a result of the analysis of PSA mRNA expression level illustrated in FIG. 14, all 9,16S-dihydroxy-10,17-octadecadiene-12,14-diynoic acid (HS3), 9,16R-dihydroxy-10,17-octadecadiene-12,14-diynoic acid (HS5), and (9Z)-16-hydroxy-9,17-octadecadiene-12,14-diynoic acid (HS7) were identified to inhibit the mRNA expression of PSA, the target gene of AR, and particularly, (9Z)-16-hydroxy-9,17-octadecadiene-12,14-diynoic acid (HS7) was determined to be most effective in inhibiting the mRNA expression of PSA.

<7-2> Analysis Result of the Level of 15-PGDH mRNA Expression

As a result of the analysis of 15-PGDH mRNA expression level, it was identified that the mRNA expression of 15-PGDH, the target gene of AR signaling is also inhibited by the above-described 3 compounds isolated and identified in the present invention.

<7-3> Analysis Result of the Level of 5αR-1/-2 mRNA Expression

Figure 16:
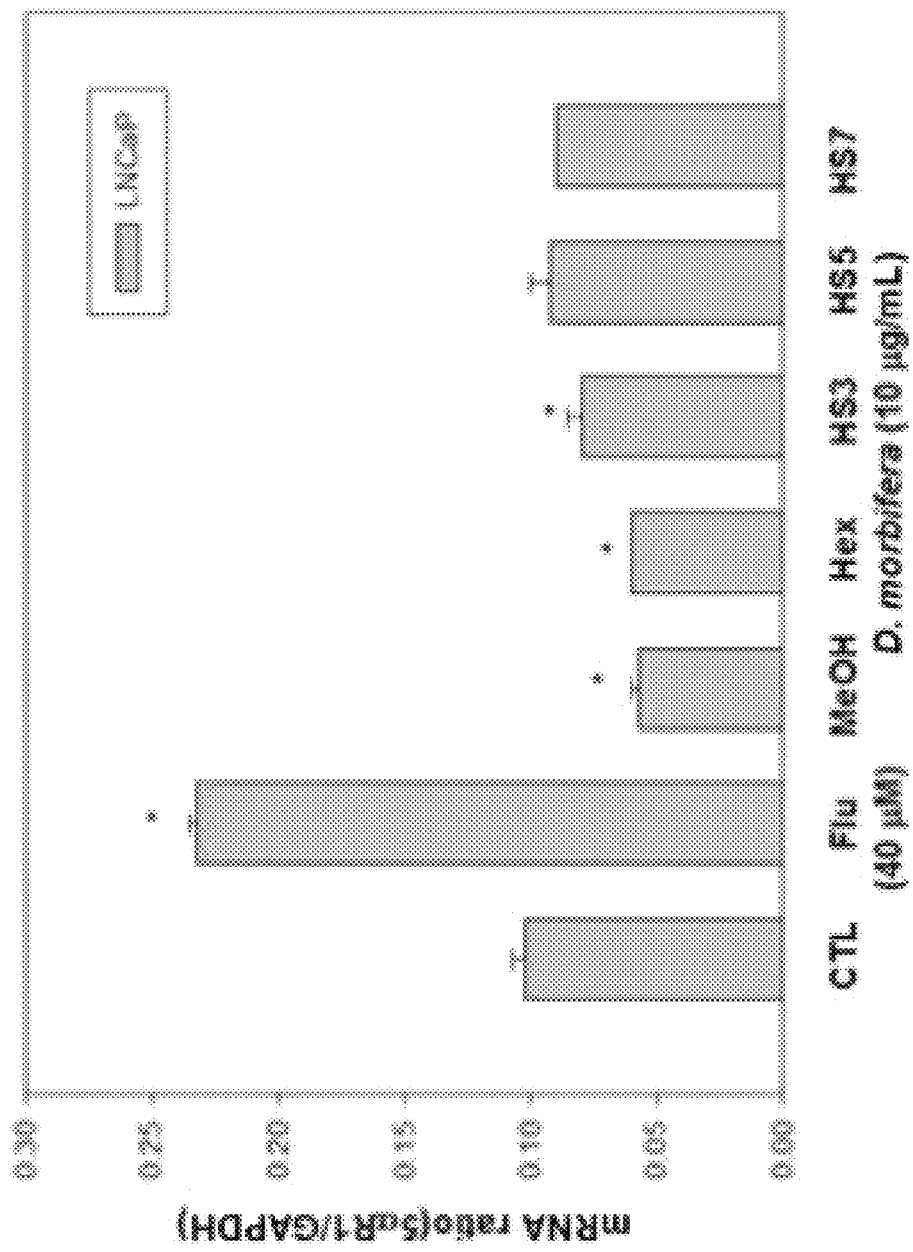
FIG. 16 illustrates the result of analysis, in which the effects of *Dendropanax morbifera* solvent extract of the present invention and 3 single compounds isolated from the *Dendropanax morbifera* hexane extract on the expression of 5αR-1 mRNA in prostate cancer cell line (LNCaP•FGC) were analyzed.
Figure 17:
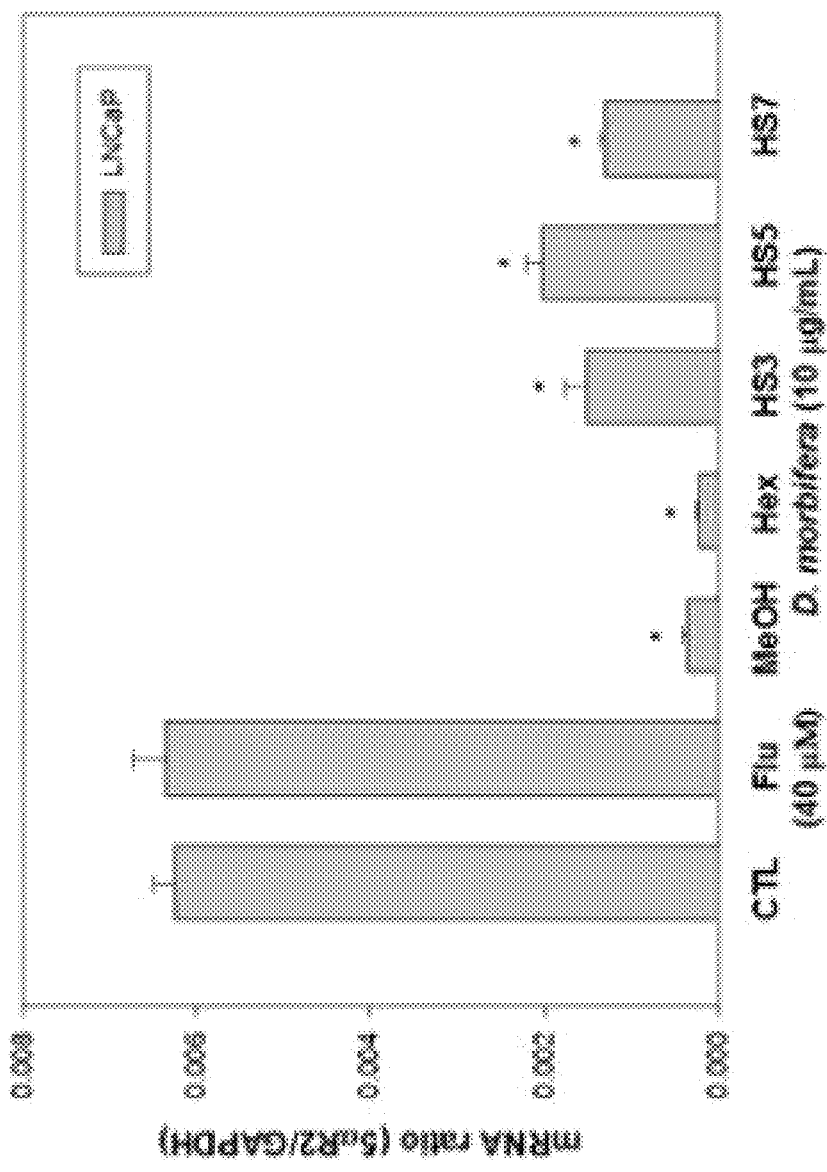
FIG. 17 illustrates the result of analysis, in which the effects of *Dendropanax morbifera* solvent extract of the present invention and 3 single compounds isolated from the *Dendropanax morbifera* hexane extract on the expression of 5αR-2 mRNA in prostate cancer cell line (LNCaP•FGC) were analyzed.
Figure 18:
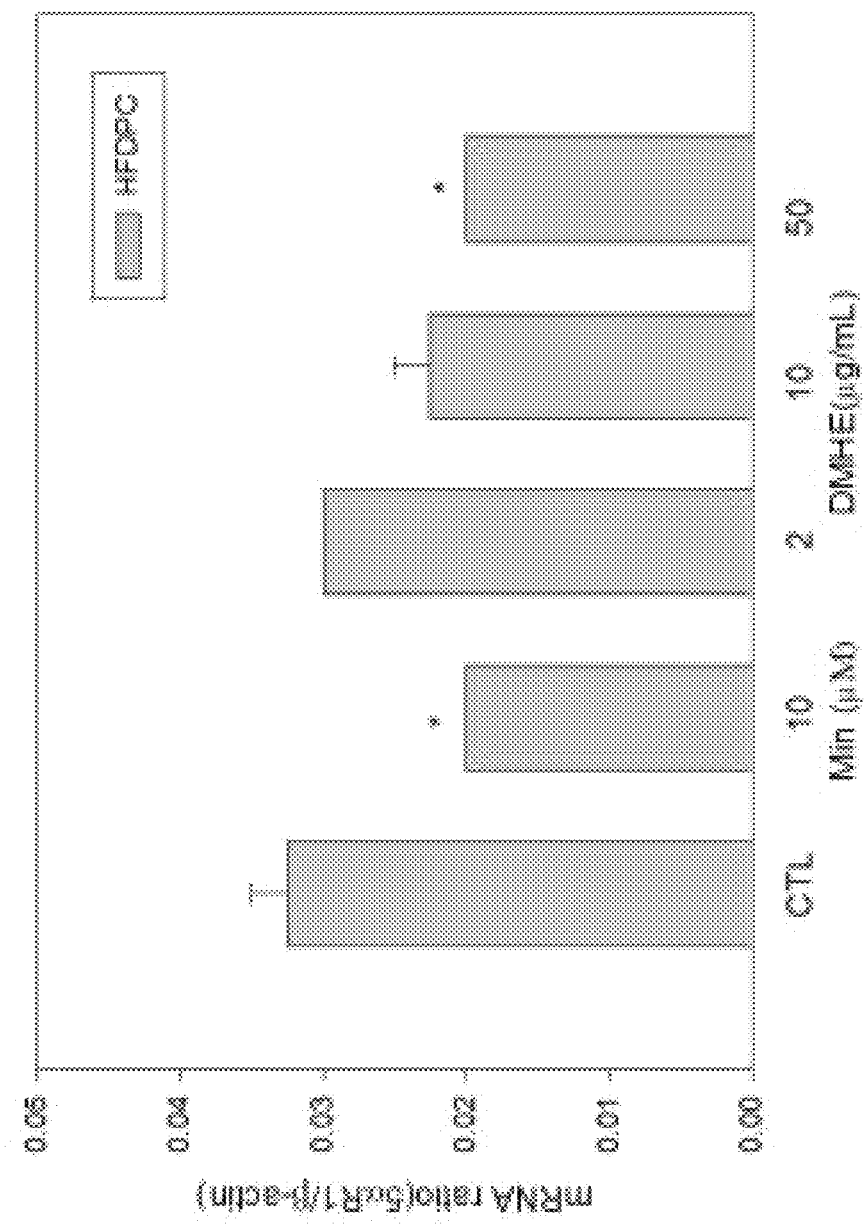
FIG. 18 illustrates the result of analysis, in which the 5αR1 mRNA expression level upon the treatment of varying concentration of *Dendropanax morbifera* hexane extract of the present invention was measured in HFDPC (human hair dermal papilla cell) that is an androgen receptor expressing cell line and used in studying the AR signaling (Min: Group treated with minoxidil, DMHE: Group treated with the *Dendropanax morbifera* hexane extract of the present invention).
Figure 19:
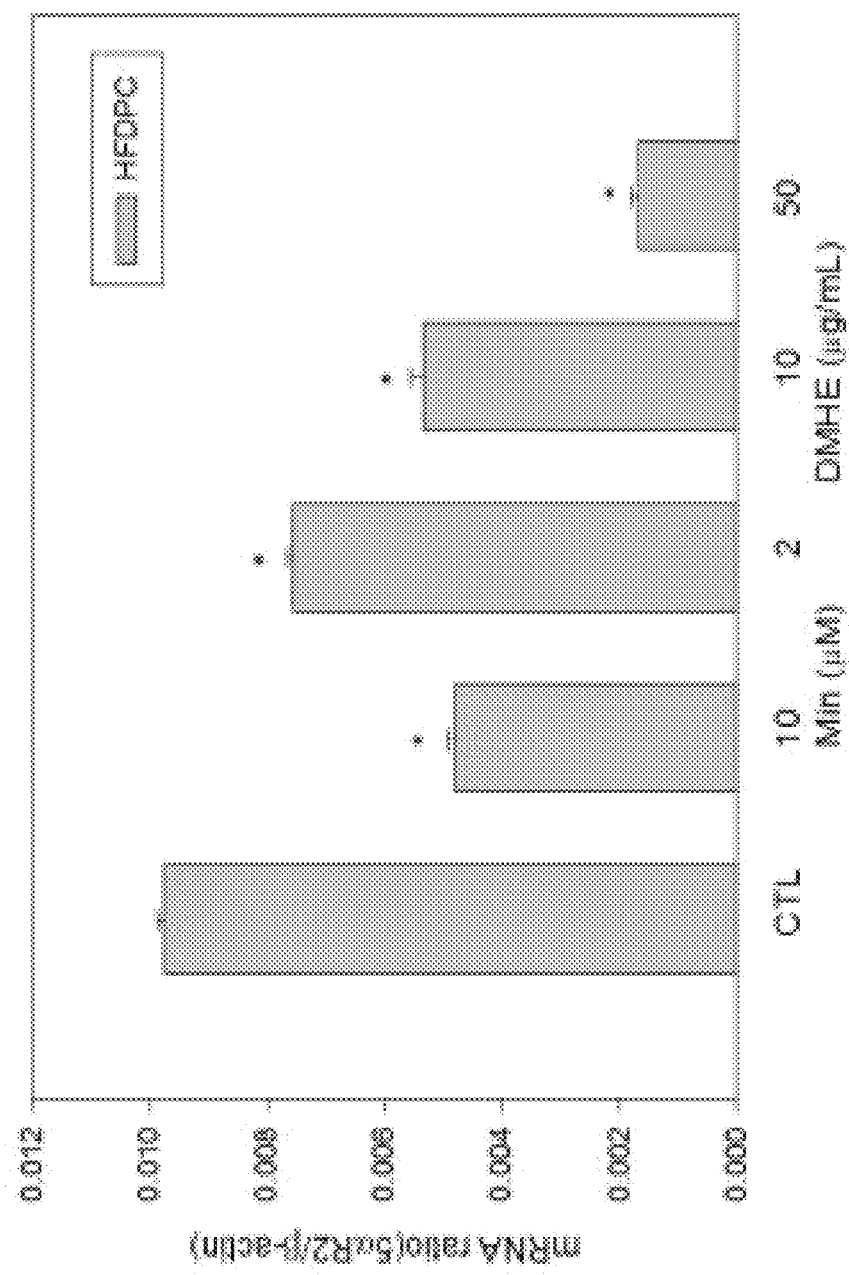
FIG. 19 illustrates the result of analysis, in which the 5αR2 mRNA expression level upon the treatment of varying concentration of *Dendropanax morbifera* hexane extract of the present invention was measured in HFDPC (human hair dermal papilla cell) (Min: Group treated with minoxidil, DMHE: Group treated with the *Dendropanax morbifera* hexane extract of the present invention).
Figure 20:
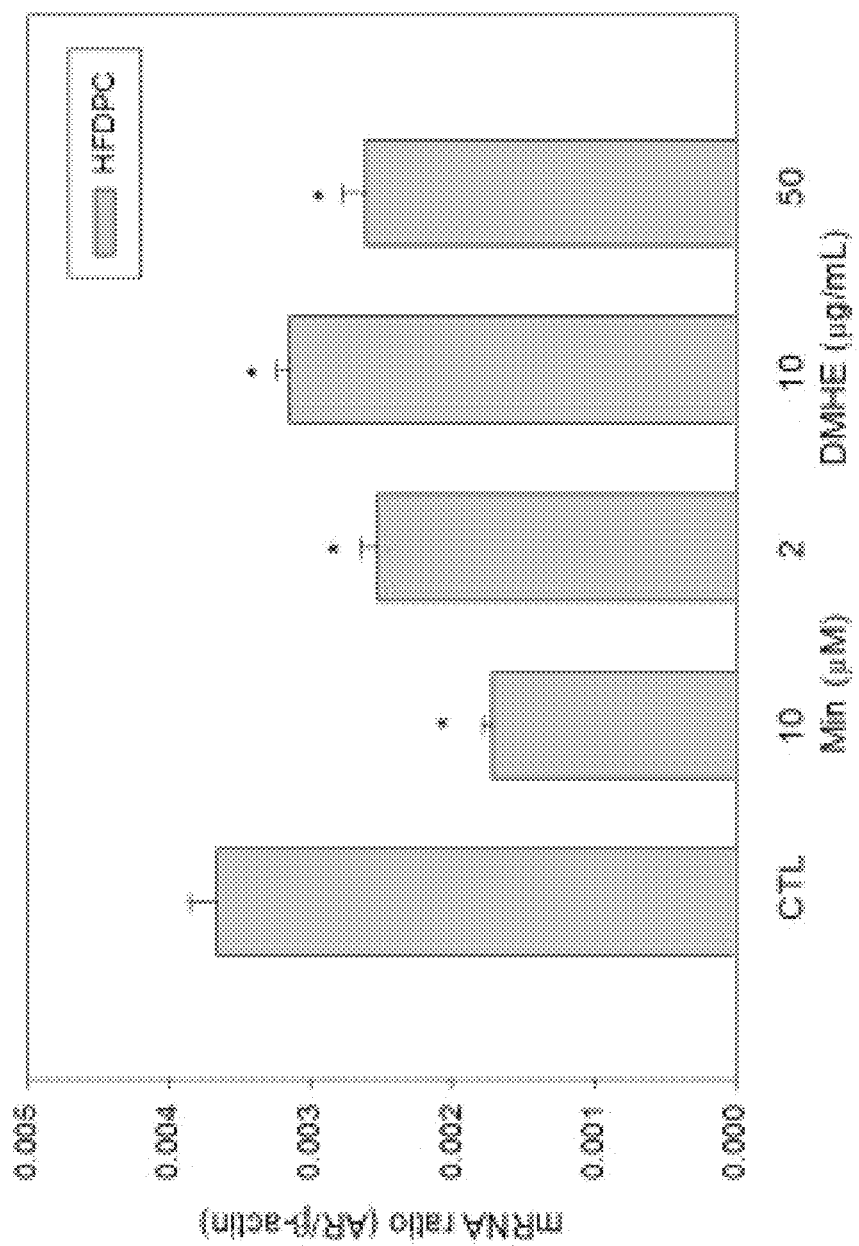
FIG. 20 illustrates the result of analysis, in which the androgen receptor (AR) mRNA expression level upon the treatment of varying concentration of *Dendropanax morbifera* hexane extract of the present invention was measured in HFDPC (human hair dermal papilla cell) (Min: Group treated with minoxidil, DMHE: Group treated with the *Dendropanax morbifera* hexane extract of the present invention).
Figure 21:
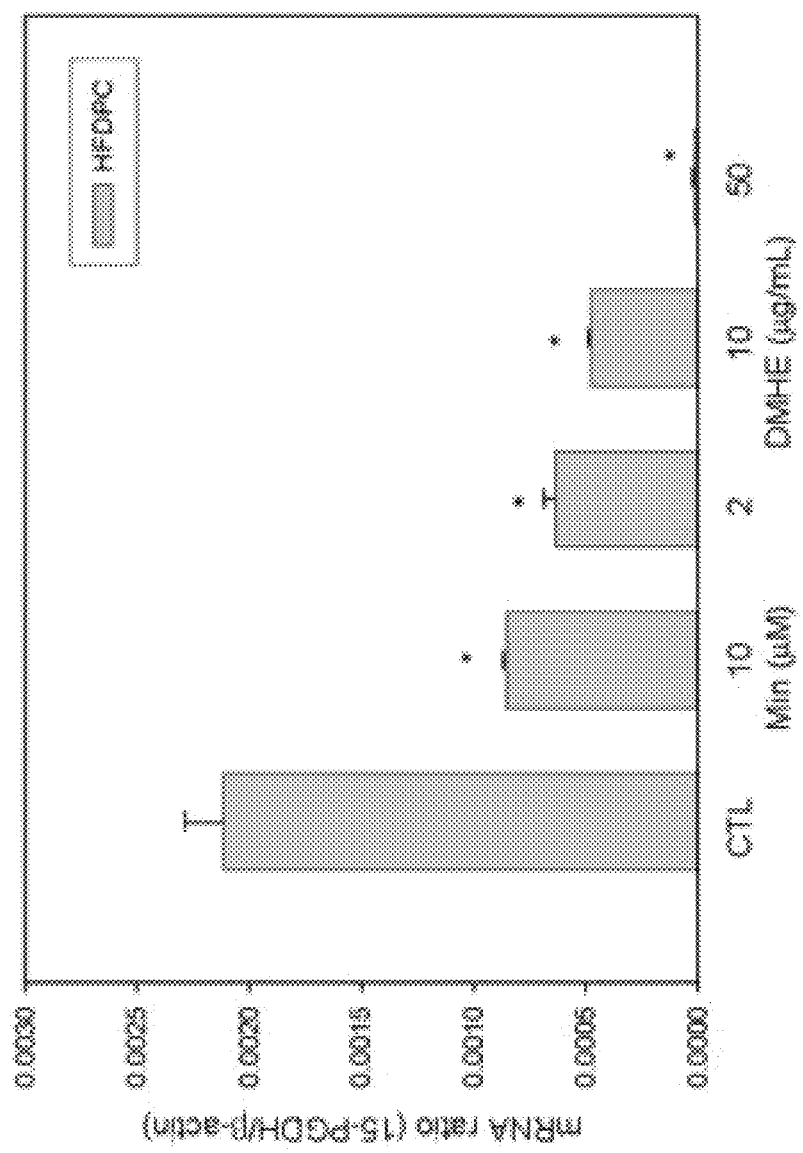
FIG. 21 illustrates the result of analysis, in which the 15-PGDH mRNA expression level upon the treatment of varying concentration of *Dendropanax morbifera* hexane extract of the present invention was measured in HFDPC (human hair dermal papilla cell) (Min: Group treated with minoxidil, DMHE: Group treated with the *Dendropanax morbifera* hexane extract of the present invention).

Furthermore, as a result of analysis of 5αR-1/-2 mRNA expression level, the *Dendropanax morbifera* extract of the present invention and the above-described 3 compounds all inhibit the levels of mRNA expressions of 5α-1/-2 (see FIGS. 16 and 17).

Therefore, through these results, the inventors identified that the *Dendropanax morbifera* hexane extract of the present invention and single compounds, 9,16S-dihydroxy-10,17-octadecadiene-12,14-diynoic acid (HS3), 9,16R-dihydroxy-10,17-octadecadiene-12,14-diynoic acid (HS5), and (9Z)-16-hydroxy-9,17-octadecadiene-12,14-diynoic acid (HS7) that are derived from the above-described extract are all possible to be used for prevention and treatment of benign prostatic hyperplasia through in vitro and in vivo experiments.

<Formulation Example 1> Preparation of Pharmaceutical Formulation

1. Preparation of Tablets

The tablets including the *Dendropanax morbifera* extract of the present invention as an active ingredient, which were obtained in Examples, were prepared by method described below.

Lactose, starch and pregelatinized corn starch were mixed with the *Dendropanax morbifera* extract, and then, granulated to powder by adding appropriate volume of purified water. After drying the granules, they were mixed with magnesium stearate and compressed to obtain tablets.

The components of the above-described tablet are listed as follow.

5.0 mg of *Dendropanax morbifera* extract
150.0 mg of Lactose BP
30.0 mg of Starch BP
15.0 mg of Pregelatinized corn starch BP
1.0 mg of Magnesium stearate 2. Preparation of Capsules The capsules including the *Dendropanax morbifera* extract of the present invention as an active ingredient were prepared by method described below.

The above-described *Dendropanax morbifera* extract of the present invention was mixed with predetermined amounts of excipient and magnesium stearate. The obtained mixture was filled in a gelatin capsule to obtain the capsules.

The components of the above-described capsule are listed as follows.

5.0 mg of *Dendropanax morbifera* extract
100.0 mg of Starch 1500
1.0 mg of Magnesium stearate BP 3. Preparation of Injection Solutions The injection solutions including the *Dendropanax morbifera* extract of the present invention as an active ingredient were prepared by method described below.

In appropriate volume of sodium chloride BP for injection, the above-described plant extract was dissolved and pH of the produced solution was adjusted to pH 3.5 by using diluted hydrochloric acid BP, and then the volume was adjusted with sodium chloride BP and mixed thoroughly. The solution was filled in a transparent glass 5 ml-type I ampule and the glass was dissolved, thereby sealing the ample under the upper lattice of air, and subsequently the ample was autoclaved at 120° C. for sterilization for 15 minutes or more to obtain the injection solution.

The components of the above-described injection solution are listed as follows.

100 μg/ml of *Dendropanax morbifera* extract
Diluted hydrochloric acid BP with pH adjusted to 3.5
Maximum amount, 1 ml of Sodium chloride BP Hitherto, the present invention was addressed mainly by the favorable exemplary embodiments thereof. An ordinary skill in the art to which the present invention belongs will understand that the present invention can be transformed and implemented without deviating from the essential properties thereof. Thus, all exemplary embodiments disclosed herein should be considered not in terms of limited aspects, but in terms of descriptive aspects. The scope of the present invention is not shown in the aforementioned description, but in the scope of request for a patent and all discrepancies existing in the equivalent scope should be regarded as included in the present invention.

The invention claimed is:

1. A method for preventing or treating benign prostatic hyperplasia, the method comprising administering a *Dendropanax morbifera* extract to a subject requiring the same.

2. The method of claim 1, wherein the *Dendropanax morbifera* extract is a crude extract of *Dendropanax morbifera*, a polar solvent soluble extract or a non-polar solvent soluble extract.

3. The method of claim 1, wherein the crude extract is an extract soluble in a solvent selected from water including purified water, methanol, ethanol, butanol, or a mixed solvent thereof.

4. The method of claim 1, wherein the non-polar solvent soluble extract is an extract soluble in hexane, chloroform, dichloromethane, or ethyl acetate.

5. The method of claim 1, wherein the *Dendropanax morbifera* extract has inhibitory activity for expression of 5a-reductase or androgen receptor (AR).

6. The method of claim 1, wherein the *Dendropanax morbifera* extract includes a 9,16S-dihydroxy-10,17-octadecadiene-12,14-diynoic acid, 9,16R-dihydroxy-10,17-octadecadiene-12,14-diynoic acid, or (9Z)-16-hydroxy-9,17-octadecadiene-12,14-diynoic acid compound.

7. A method for preventing or treating benign prostatic hyperplasia, the method comprising administering to a subject in need thereof 9,16S-dihydroxy-10,17-octadecadiene-12,14-diynoic acid, 9,16R-dihydroxy-10,17-octadecadiene-12,14-diynoic acid, or (9Z)-16-hydroxy-9,17-octadecadiene-12,14-diynoic acid compound as an active ingredient.

8. The method of claim 7, wherein the compound is isolated and purified from a *Dendropanax morbifera* hexane extract.

9. The method of claim 7, wherein the compound inhibits and decreases mRNA expression of prostate specific antigen (PSA), 15-PGDH, and 5aR-2 (5a-reductase type 2).

* * * * *